United States Patent
Mitchell et al.

(10) Patent No.: US 11,773,434 B2
(45) Date of Patent: Oct. 3, 2023

(54) ASSESSING TRANSPLANT COMPLICATION RISK WITH TOTAL CELL-FREE DNA

(71) Applicant: The Medical College of Wisconsin, Inc., Milwaukee, WI (US)

(72) Inventors: Aoy Tomita Mitchell, Elm Grove, WI (US); Michael Mitchell, Elm Grove, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 276 days.

(21) Appl. No.: 16/623,707

(22) PCT Filed: Jun. 20, 2018

(86) PCT No.: PCT/US2018/038598
§ 371 (c)(1),
(2) Date: Dec. 17, 2019

(87) PCT Pub. No.: WO2018/237075
PCT Pub. Date: Dec. 27, 2018

(65) Prior Publication Data
US 2021/0139969 A1    May 13, 2021

Related U.S. Application Data

(60) Provisional application No. 62/572,556, filed on Oct. 15, 2017, provisional application No. 62/522,533, filed on Jun. 20, 2017.

(51) Int. Cl.
*C12Q 1/6858* (2018.01)

(52) U.S. Cl.
CPC ..... *C12Q 1/6858* (2013.01); *C12Q 2535/101* (2013.01)

(58) Field of Classification Search
None
See application file for complete search history.

(56) References Cited

U.S. PATENT DOCUMENTS

| | | | |
|---|---|---|---|
| 5,180,812 A | 1/1993 | Dower et al. | |
| 5,319,071 A | 6/1994 | Dower et al. | |
| 5,464,937 A | 11/1995 | Sims et al. | |
| 5,488,032 A | 1/1996 | Dower et al. | |
| 5,492,888 A | 2/1996 | Dower et al. | |
| 5,569,582 A | 10/1996 | Tavernarakis et al. | |
| 5,595,890 A | 1/1997 | Newton et al. | |
| 5,645,988 A | 7/1997 | Vande et al. | |
| 7,718,370 B2 | 5/2010 | Dhallan | |
| 8,609,338 B2 | 12/2013 | Mitchell et al. | |
| 9,290,815 B2 | 3/2016 | Di Pasquale et al. | |
| 10,385,396 B2 | 8/2019 | Mitchell et al. | |
| 10,472,680 B2 | 11/2019 | Mitchell et al. | |
| 2003/0148301 A1 | 8/2003 | Aono et al. | |
| 2006/0014179 A1 | 1/2006 | Roberts | |
| 2006/0088871 A1 | 4/2006 | Finkelstein et al. | |
| 2007/0134658 A1 | 6/2007 | Bohmer | |
| 2008/0020390 A1 | 1/2008 | Mitchell et al. | |
| 2009/0087847 A1 | 4/2009 | Lo et al. | |
| 2010/0326218 A1 | 12/2010 | Boeckh et al. | |
| 2011/0110931 A1 | 5/2011 | Matsui | |
| 2012/0010085 A1 | 1/2012 | Rava et al. | |
| 2012/0021442 A1 | 1/2012 | Buhimschi et al. | |
| 2012/0034685 A1 | 2/2012 | Sparks et al. | |
| 2012/0270212 A1 | 10/2012 | Rabinowitz et al. | |
| 2013/0071844 A1 | 3/2013 | Makino et al. | |
| 2013/0143219 A1 | 6/2013 | Mitchell et al. | |
| 2013/0231252 A1 | 9/2013 | Mitchell et al. | |
| 2013/0323727 A1 | 12/2013 | Huang et al. | |
| 2013/0344066 A1 | 12/2013 | Faham et al. | |
| 2014/0045181 A1 | 2/2014 | Lo et al. | |
| 2015/0056617 A1 | 2/2015 | Whitt et al. | |
| 2015/0086477 A1 | 3/2015 | Mitchell et al. | |
| 2015/0167077 A1 | 6/2015 | Fehr et al. | |
| 2015/0246103 A1 | 9/2015 | Hazout | |
| 2016/0053320 A1 | 2/2016 | Schuh et al. | |
| 2016/0115541 A1 | 4/2016 | Schutz et al. | |
| 2016/0145682 A1 | 5/2016 | Woodward et al. | |
| 2016/0186239 A1 | 6/2016 | Sinha | |
| 2017/0114411 A1 | 4/2017 | Mitchell et al. | |
| 2018/0142296 A1 | 5/2018 | Mitchell et al. | |
| 2018/0303870 A1 | 10/2018 | Golobish et al. | |
| 2018/0320239 A1 | 11/2018 | Babiarz et al. | |
| 2018/0371531 A1 | 12/2018 | Quake et al. | |
| 2019/0153521 A1 | 5/2019 | Mitchell et al. | |
| 2019/0153525 A1 | 5/2019 | Mitchell et al. | |

(Continued)

FOREIGN PATENT DOCUMENTS

| | | |
|---|---|---|
| BR | 112017023232 A2 | 8/2018 |
| CA | 2875281 A1 | 12/2013 |

(Continued)

OTHER PUBLICATIONS

Extended European Search Report for Application No. 18820195.8, dated Jan. 27, 2021.
International Search Report and Written Opinion for Application No. PCT/US2018/038598 dated Sep. 7, 2018.
International Preliminary Report on Patentability for Application No. PCT/US2018/038598 dated Jan. 2, 2020.
GenBank Submission; Accession No. BC093685, version BC093685. 1. *Homo sapiens* placenta-specific 4, mRNA (cDNA clone MGC:120720 Image:7939530), complete cds. Strausberg et al.; Jan. 18, 2007. 2 Pages.

(Continued)

*Primary Examiner* — Teresa E Strzelecka
(74) *Attorney, Agent, or Firm* — Wolf, Greenfield & Sacks, P.C.

(57) ABSTRACT

This invention relates to methods and compositions for assessing an amount of total cell-free DNA, such as from a transplant subject. The methods and composition provided herein can be used to determine risk of complications following transplantation, including infection, cardiac arrest, and death, in a subject.

9 Claims, 20 Drawing Sheets

(56) References Cited

U.S. PATENT DOCUMENTS

| | | | |
|---|---|---|---|
| 2019/0211376 | A1 | 7/2019 | Quake et al. |
| 2019/0360033 | A1 | 11/2019 | Stamm et al. |
| 2019/0367972 | A1 | 12/2019 | Mitchell et al. |
| 2020/0032340 | A1 | 1/2020 | Mitchell et al. |
| 2020/0109449 | A1 | 4/2020 | Stamm et al. |
| 2020/0121718 | A1 | 4/2020 | Novik et al. |
| 2020/0141925 | A1 | 5/2020 | Liaw et al. |
| 2020/0165678 | A1 | 5/2020 | Mitchell et al. |
| 2020/0181681 | A1 | 6/2020 | Mitchell et al. |
| 2021/0139983 | A1 | 5/2021 | Mitchell et al. |
| 2021/0139988 | A1 | 5/2021 | Mitchell et al. |
| 2021/0301320 | A1 | 9/2021 | Mitchell et al. |
| 2022/0145391 | A1 | 5/2022 | Mitchell et al. |
| 2022/0267849 | A1 | 8/2022 | Mitchell et al. |
| 2022/0356522 | A1 | 11/2022 | Mitchell et al. |

FOREIGN PATENT DOCUMENTS

| | | |
|---|---|---|
| CN | 102892901 A | 1/2013 |
| CN | 107849604 A | 3/2018 |
| CN | 109661476 A | 4/2019 |
| EA | 201792389 A1 | 5/2018 |
| EP | 1325963 A1 | 7/2003 |
| EP | 1325963 B1 | 9/2006 |
| EP | 2551356 A1 | 1/2013 |
| JP | 2004-121087 A | 4/2004 |
| JP | 2013-509883 A | 3/2013 |
| JP | 2016-502849 A | 2/2016 |
| WO | WO 96/23067 A1 | 8/1996 |
| WO | WO 99/37773 A1 | 7/1999 |
| WO | WO 2004/078999 A1 | 9/2004 |
| WO | WO 2011/015944 A2 | 2/2011 |
| WO | WO 2011/057061 A1 | 5/2011 |
| WO | WO 2011/094646 A1 | 8/2011 |
| WO | WO 2011/118603 A1 | 9/2011 |
| WO | WO 2012/122374 A2 | 9/2012 |
| WO | WO 2013/159035 A2 | 10/2013 |
| WO | WO 2014/099919 A2 | 6/2014 |
| WO | WO 2014/143989 A1 | 9/2014 |
| WO | WO 2014/194113 A2 | 12/2014 |
| WO | WO 2015/035177 A1 | 3/2015 |
| WO | WO 2015/069933 A1 | 5/2015 |
| WO | WO 2015/138997 A1 | 9/2015 |
| WO | WO 2015/169947 A1 | 11/2015 |
| WO | WO 2015/178978 A2 | 11/2015 |
| WO | WO 2016/001411 A1 | 1/2016 |
| WO | WO 2016/028316 A1 | 2/2016 |
| WO | WO 2016/063122 A1 | 4/2016 |
| WO | WO 2016/123698 A1 | 8/2016 |
| WO | WO 2016/176662 A1 | 11/2016 |
| WO | WO 2017/011329 A1 | 1/2017 |
| WO | WO 2017/091865 A1 | 6/2017 |
| WO | WO 2017/190106 A1 | 11/2017 |
| WO | WO 2018/085597 A1 | 5/2018 |
| WO | WO 2018/085603 A1 | 5/2018 |
| WO | WO 2018/119422 A1 | 6/2018 |
| WO | WO 2018/237078 A1 | 12/2018 |
| WO | WO 2018/237081 A1 | 12/2018 |
| WO | WO 2019/006561 A1 | 1/2019 |
| WO | WO 2019/008408 A1 | 1/2019 |
| WO | WO 2019/053243 A1 | 3/2019 |
| WO | WO 2019/109053 A1 | 6/2019 |
| WO | WO 2019/118926 A1 | 6/2019 |
| WO | WO 2020/131955 A1 | 6/2020 |
| WO | WO 2020/206290 A1 | 10/2020 |

OTHER PUBLICATIONS

GenBank Submission; Accession No. NG_012386, version NG_012386. 1. *Homo sapiens* TSC complex subunit 1 (TSC1), RefSeqGene (LRG_486) on chromosome 9. Huang et al.; Sep. 21, 2020. 20 Pages.

GenBank Submission; Accession No. NG_007524, version NG_007524. 2. *Homo sapiens* KRAS proto-oncogene, GTPase (KRAS), RefSeqGene (LRG_344) on chromosome 12. Gripp et al.; Aug. 16, 2020. 16 Pages.

[No Author Listed], Google search results for "The Journal of Heart and Lung Transplantation Apr. 2012. vol. 31, Issue 4, Supplement, pp. A1-A4, S1-S310.".

[No Author Listed], Nucleic acid sequence search reports AC: 151794. Oct. 7, 1997. Sequence 6 from Patent U.S. Pat. No. 5,645,988, Accession I51796.

Adamek et al., A fast and simple method for detecting and quantifying donor-derived cell-free DNA in sera of solid organ transplant recipients as a biomarker for graft function. Clin Chem Lab Med. Jul. 1, 2016;54(7):1147-55. doi: 10.1515/cclm-2015-0622.

Ayyadevara et al., Discrimination of primer 3'—nucleotide mismatch by taq DNA polymerase during polymerase chain reaction. Anal Biochem. Aug. 15, 2000; 284(1):11-8.

Bai et al., Detection and quantification of heteroplasmic mutant mitochondrial DNA by real-time amplification refractory mutation system quantitative PCR analysis: a single-step approach. Clin Chem. Jun. 2004;50(6):996-1001. Epub Apr. 8, 2004.

Bergallo et al., A novel TaqMAMA assay for allelic discrimination of TLR9 rs352140 polymorphism. J Virol Methods. May 2017;243:25-30. doi: 10.1016/j.jviromet.2017.01.015. Epub Jan. 28, 2017.

Bergallo et al., Evaluation of IFN-γ polymorphism+874 T/A in patients with recurrent tonsillitis by PCR real time mismatch amplification mutation assay (MAMA real time PCR). Cytokine. Feb. 2015; 71(2):278-82. Epub Dec. 2014.

Board et al., Detection of PIK3CA mutations in circulating free DNA in patients with breast cancer. Breast Cancer Res Treat. Apr. 2010; 120(2):461-7. doi: 10.1007/s10549-010-0747-9. Epub Jan. 28, 2010.

Board et al., Multiplexed assays for detection of mutations in PIK3CA. Clin Chem. Apr. 2008; 54(4):757-60.

Burgstaller et al., Mitochondrial DNA heteroplasmy in ovine fetuses and sheep cloned by somatic cell nuclear transfer. BMC Dev Biol. Dec. 21, 2007;7:141.

Castleberr et al., Quantification of Circulating Cell-Free DNA in Pediatric Heart Transplant Recipients. Journal of Heart and Lung Transplantation. Apr. 1, 2011; 30(4):S139. ISSN: 1053-2498, DOI: 10.1016/j.healun.2011.01.415.

Chiu et al., Effects of blood-processing protocols on fetal and total DNA quantification in maternal plasma. Clin Chem. Sep. 2001;47(9):1607-13. PubMed PMID: 11514393.

Chiu et al., Noninvasive prenatal exclusion of congenital adrenal hyperplasia by maternal plasma analysis: a feasibility study. Clin Chem. May 2002;48(5):778-80.

Chu et al., A novel approach toward the challenge of accurately quantifying fetal DNA in maternal plasma. Prenat Diagn. Dec. 2010;30(12-13):1226-9. doi: 10.1002/pd.2656.

Daly, Circulating donor-derived cell-free DNA: a true biomarker for cardiac allograft rejection? Ann Transl Med. Mar. 2015;3(4):47. doi:10.3978/j.issn.2305-5839.2015.01.35.

Dastsooz et al., Multiplex ARMS PCR to Detect 8 Common Mutations of ATP7B Gene in Patients With Wilson Disease. Hepat Mon. May 16, 2013;13(5):e8375. doi: 10.5812/hepatmon.8375. eCollection 2013.

De Vlaminck et al., Circulating cell-free DNA enables noninvasive diagnosis of heart transplant rejection. Sci Transl Med. Jun. 18, 2014;6(241):241ra77. doi: 10.1126/scitranslmed.3007803.

Dey et al., A plasma telomeric cell-free DNA level in unaffected women with BRCA1 or/and BRCA2 mutations: a pilot study. Oncotarget. Dec. 29, 2017;9(3):4214-4222. doi: 10.18632/oncotarget.23767. eCollection Jan. 9, 2018.

García Moreira et al., Cell-free DNA as a noninvasive acute rejection marker in renal transplantation. Clin Chem. Nov. 2009;55(11):1958-66. doi:10.1373/clinchem.2009.129072. Epub Sep. 3, 2009.

Ghanta et al., Non-invasive prenatal detection of trisomy 21using tandem single nucleotide polymorphisms. PLoS One. Oct. 8, 2010;5(10):e13184. doi: 10.1371/journal.pone.0013184.

Gielis et al., Plasma donor-derived cell-free DNA kinetics after kidney transplantation using a single tube multiplex PCR assay. PLoS One. 2018; 13(12): e0208207.

(56) References Cited

OTHER PUBLICATIONS

Glaab et al., A novel assay for allelic discrimination that combines the fluorogenic 5' nuclease polymerase chain reaction (TaqMan) and mismatch amplification mutation assay. Mutat Res. Nov. 29, 1999;430(1):1-12.

Gordon et al., An Algorithm Measuring Donor Cell-Free DNA in Plasma of Cellular and Solid Organ Transplant Recipients That Does Not Require Donor or Recipient Genotyping. Front Cardiovasc Med. Sep. 22, 2016;3:33. eCollection 2016.

Gotoh et al., Prediction of MYCN amplification in neuroblastoma using serum DNA and real-time quantitative polymerase chain reaction. J Clin Oncol. Aug. 1, 2005;23(22):5205-10. PubMed PMID: 16051962.

Grskovic et al., Validation of a Clinical-Grade Assay to Measure Donor-Derived Cell-Free DNA in Solid Organ Transplant Recipients. J Mol Diagn. Nov. 2016;18(6):890-902. doi: 10.1016/j.jmoldx.2016.07.003. Epub Oct. 7, 2016.

Guedj et al., A refined molecular taxonomy of breast cancer. Oncogene. Mar. 1, 2012;31(9):1196-206. doi: 10.1038/onc.2011.301. Epub Jul. 25, 2011.

Hidestrand et al., Highly sensitive noninvasive cardiac transplant rejection monitoring using targeted quantification of donor-specific cell-free deoxyribonucleic acid. J Am Coll Cardiol. Apr. 1, 2014;63(12):1224-1226. doi:10.1016/j.jacc.2013.09.029. Epub Oct. 16, 2013.

Hidestrand et al., Highly Sensitive Transplant Rejection Surveillance Using Targeted Detection of Donor Specific Cell Free DNA. J Heart Lung Transplant. Apr. 2012; 31(4):S91-2.

Hidestrand et al., Influence of temperature during transportation on cellfree DNA analysis. Fetal Diagn Ther. 2012; 31:122-128.

Hidestrand et al., Quantification of Circulating Donor Specific Cell Free DNA is an Exquisitely Sensitive Non-Invasive Indicator of Injury to the Donor Heart. J Heart Lung Transplant. 2013; 32: S101-S102.

Hoerning et al., Quantitative real-time ARMS-qPCR for mitochondrial DNA enables accurate detection of microchimerism in renal transplant recipients. Pediatr Transplant. Dec. 2011;15(8):809-18. doi: 10.1111/j.1399-3046.2011.01581.x. Epub Oct. 4, 2011.

Hou et al., Application of tetra primer ARMS-PCR approach for detection of Fusarium graminearum genotypes with resistance to carbendazim. Australian Plant Pathology. Jan. 1, 2013; 42(l):73-8.

Jordan et al., Donor-derived Cell-free DNA Identifies Antibody-mediated Rejection in Donor Specific Antibody Positive Kidney Transplant Recipients. Transplant Direct. 2018;4(9):e379.

Khush et al., Circulating cell-free DNA as a non-invasive marker of pediatric heart transplant rejection and immunosuppressive treatment. J Heart Lung Transplantation. Apr. 2016. 35(4):Abstract 181. S75.

Kindel et al., Early Changes in Donor Fraction Cell-free DNA in Newly Transplanted Heart Transplant Patients. ISHLT DF cfDNA declanation poster. 2018. 1 Page.

Kuo et al., Preimplantation and prenatal genetic diagnosis of aromatic L-amino acid decarboxylase deficiency with an amplification refractory mutation system-quantitative polymerase chain reaction. Taiwan J Obstet Gynecol. Dec. 2011;50(4):468-73. doi: 10.1016/j.tjog.2011.10.012.

Lajin et al., A quadruplex tetra-primer ARMS-PCR method for the simultaneous detection of TP53 Arg72Pro, IVS3 16bp Del/Ins and IVS6+62A?G, and NQO1 C609T polymorphisms. Gene. Aug. 10, 2012; 504(2):268-73. Epub May 23, 2012.

Lang et al., Optimized allele-specific real-time PCR assays for the detection of common mutations in KRAS and BRAF. J Mol Diagn. Jan. 2011;13(1):23-8. doi: 10.1016/j.jmoldx.2010.11.007. Epub Dec. 23, 2010.

Lee et al., Allele-Specific Quantitative PCR for Accurate, Rapid, and Cost-Effective Genotyping. Hum Gene Ther. Jun. 2016;27(6):425-35. doi: 10.1089/hum.2016.011. Epub Mar. 17, 2016.

Lefebure et al., Prognostic value of circulating mutant DNA in unresectable metastatic colorectal cancer. Ann Surg. Feb. 2010;251(2):275-80. doi: 10.1097/SLA.0b013e3181c35c87.

Levy et al., Analysis of Cell-Free DNA to Assess Risk of Tumoremia Following Endoscopic Ultrasound Fine-Needle Aspiration of Pancreatic Adenocarcinomas. Clin Gastroenterol Hepatol. Oct. 2018;16(10):1632-1640.e1. doi: 10.1016/j.cgh.2018.02.048. Epub Mar. 8, 2018.

Li et al., Multiplex co-amplification of 24 retinoblastoma gene exons after pre-amplification by long-distance PCR. Nucleic Acids Res. Feb. 1, 1996;24(3):538-9.

Liu et al., Comparison of next-generation sequencing systems. J Biomed Biotechnol. 2012;2012:1-11. doi: 10.1155/2012/251364. Epub Jul. 5, 2012.

Lo et al., Plasma placental RNA allelic ratio permits noninvasive prenatal chromosomal aneuploidy detection. Nat Med. Feb. 2007;13(2):218-23. doi: 10.1038/nml530. Epub Jan. 7, 2007.

Lo, Transplantation monitoring by plasma DNA sequencing. Clin Chem. Jul. 2011;57(7):941-2. doi: 10.1373/clinchem.2011.166686. PubMed PMID: 21566070.

Mak et al., Rapid diagnosis of Wilson disease by a 28-mutation panel: real-time amplification refractory mutation system in diagnosing acute Wilsonian liver failure. Clin Chim Acta. Dec. 2008;398(l-2):39-42. doi: 10.1016/j.cca.2008.08.002. Epub Aug. 8, 2008.

Manage et al., Genotyping single nucleotide polymorphisms in human genomic DNA with an automated and self-contained PCR cassette. J Mol Diagn. Sep. 2014;16(5):550-557. doi:10.1016/j.jmoldx.2014.04.004. Epub Jul. 2, 2014.

Mehra et al., Gene expression profiles and B-type natriuretic peptide elevation in heart transplantation: more than a hemodynamic marker. Circulation. Jul. 4, 2006;114(1 Suppl):I21-6.

Mehra et al., International Society for Heart and Lung Transplantation working formulation of a standardized nomenclature for cardiac allograft vasculopathy-2010.J Heart Lung Transplant. Jul. 2010;29(7):717-27. doi: 10.1016/j.healun.2010.05.017.

Myers et al., ACB-PCR quantification of somatic oncomutation. Methods Mol Biol. 2014;1105:345-63. doi:10.1007/978-1-62703-739-6_27.

Newton et al., Analysis of any point mutation in DNA. The amplification refractory mutation system (ARMS). Nucleic Acids Res. Apr. 11, 1989;17(7):2503-16. doi: 10.1093/nar/17.7.2503.

Oeth et al., Qualitative and quantitative genotyping using single base primer extension coupled with matrix-assisted laser desorption/ionization time-of-flight mass spectrometry (MassARRAY®). Methods Mol. Biol. 2009; 578:307-43.

Parsons et al., Allele-specific competitive blocker-PCR detection of rare base substitution. Methods Mol Biol. 2005;291:235-45.

Price et al., Cost-effective interrogation of single nucleotide polymorphisms using the mismatch amplification mutation assay and capillary electrophoresis. Electrophoresis. Dec. 2010;31(23-24):3881-8. doi: 10.1002/elps.201000379.

Quail et al., A tale of three next generation sequencing platforms: comparison of Ion torrent, pacific biosciences and illumina MiSeq sequencers. BMC Genomics. Jul. 24, 2012;13:341. doi: 10.1186/1471-2164-13-341.

Ragalie et al., Description of Longitudinal Measurement of Donor Fraction of Cell-Free DNA and Correlation to Clinical Outcomes. ISHLT poster. 2018. 1 Page.

Ragalie et al., Noninvasive Assay for Donor Fraction of Cell-Free DNA in Pediatric Heart Transplant Recipients. J Am Coll Cardiol. Jun. 26, 2018;71(25):2982-2983. doi: 10.1016/j.jacc.2018.04.026.

Roedder et al., Biomarkers in solid organ transplantation: establishing personalized transplantation medicine. Genome Med. Jun. 8, 2011;3(6):37.

Saukkonen et al., Cell-free plasma DNA as a predictor of outcome in severe sepsis and septic shock. Clin Chem. Jun. 2008;54(6):1000-7. doi: 10.1373/clinchem.2007.101030. Epub Apr. 17, 2008. PubMed PMID: 18420731.

Schnittger et al., Development and validation of a real-time quantification assay to detect and monitor BRAFV600E mutations in hairy cell leukemia. Blood. Mar. 29, 2012;119(13):3151-4. doi: 10.1182/blood-2011-10-383323. Epub Feb. 13, 2012.

Sheffield et al., Attachment of a 40-base-pair G + C-rich sequence (GC-clamp) to genomic DNA fragments by the polymerase chain reaction results in improved detection of single-base changes. Proc Natl Acad Sci U S A. Jan. 1989;86(1):232-6.

(56) References Cited

OTHER PUBLICATIONS

Shi et al., Development of a single multiplex amplification refractory mutation system PCR for the detection of rifampin-resistant Mycobacterium tuberculosis. Gene. Nov. 1, 2013; 530(1):95-9. Epub Aug. 19, 2013.
Sigdel et al., A rapid noninvasive assay for the detection of renal transplant injury. Transplantation. Jul. 15, 2013;96(1):97-101. doi: 10.1097/TP.0b013e318295ee5a.
Singh et al., Aspergillus infections in transplant recipients. Clin Microbiol Rev. Jan. 2005;18(1):44-69.
Snyder et al., Universal noninvasive detection of solid organ transplant rejection. Proc Natl Acad Sci U S A. Apr. 12, 2011;108(15):6229-34. doi: 10.1073/pnas.1013924108. Epub Mar. 28, 2011. PubMed PMID: 21444804; PubMed Central PMCID: PMC3076856.
Sparks et al., Noninvasive prenatal detection and selective analysis of cell-free DNA obtained from maternal blood: evaluation for trisomy 21 and trisomy 18. Am J Obstet Gynecol. Apr. 2012;206(4):319.e1-9. doi: 10.1016/j.ajog.2012.01.030. Epub Jan. 26, 2012.
Sparks et al., Selective analysis of cell-free DNA in maternal blood for evaluation of fetal trisomy. Prenat Diagn. Jan. 2012;32(1):3-9. Epub Jan. 6, 2012.
Stein, Next-Generation Sequencing Update. Genetic Engineering & Biotechnology News. Sep. 1, 2008; 28(15). https://www.genengnews.com/magazine/97/next-generation-sequencing-update/.
Steinborn et al., Coexistence of Bos taurus and B. indicus mitochondrial DNAs in nuclear transfer-derived somatic cattle clones. Genetics. Oct. 2002;162(2):823-9.
Stemmer et al., Use of magnetic beads for plasma cell-free DNA extraction: toward automation of plasma DNA analysis for molecular diagnostics. Clin Chem. Nov. 2003;49(11):1953-5. PubMed PMID: 14578335.
Strohmeier et al., Multiplex genotyping of KRAS point mutations in tumor cell DNA by allele-specific real-time PCR on a centrifugal microfluidic disk segment. Microchimica Acta. 2014;181 (13-14):1681-88.
Suzuki et al., Characterization of circulating DNA in healthy human plasma. Clin Chim Acta. Jan. 2008;387(1-2):55-8. doi: 10.1016/j.cca.2007.09.001. Epub Sep. 8, 2007.
Swinkels et al., Effects of blood-processing protocols on cell-free DNA quantification in plasma. Clin Chem. Mar. 2003;49(3):525-6. PubMed PMID: 12600978.
Taira et al., Quantitative monitoring of single nucleotide mutations by allele-specific quantitative PCR can be used for the assessment of minimal residual disease in patients with hematological malignancies throughout their clinical course. Clin Chim Acta. Jan. 14, 2011;412(1-2):53-8. Doi 10.1016/j.cca.2010.09.011. Epub Sep. 16, 2010.
Takai et al., Clinical utility of circulating tumor DNA for molecular assessment in pancreatic cancer. Sci Rep. Dec. 16, 2015;5:18425. doi: 10.1038/srep18425.
Tamkovich et al., Circulating nucleic acids in blood of healthy male and female donors. Clin Chem. Jul. 2005;51(7):1317-9. PubMed PMID: 15976134.
Thierry et al., Clinical validation of the detection of KRAS and BRAF mutations from circulating tumor DNA. Nat Med. Apr. 2014;20(4):430-5. doi: 10.1038/nm.3511. Epub Mar. 23, 2014.
Tomita-Mitchell et al., Human gene copy number spectra analysis in congenital heart malformations. Physiol Genomics. May 1, 2012;44(9):518-41. doi: 10.1152/physiolgenomics.00013.2012. Epub Feb. 7, 2012.
Tong et al., Diagnostic developments involving cell-free (circulating) nucleic acids. Clin Chim Acta. Jan. 2006;363(1-2):187-96. Epub Aug. 26, 2005. Review. PubMed PMID: 16126188.
Van Orsouw et al., Rapid design of denaturing gradient-based two-dimensional electrophoretic gene mutational scanning tests. Nucleic Acids Res. May 15, 1998;26(10):2398-406.
Vannucchi et al., A quantitative assay for JAK2(V617F) mutation in myeloproliferative disorders by ARMS-PCR and capillary electrophoresis. Leukemia. Jun. 2006;20(6):1055-60.
Veseloskva, The use of cell-free nucleic acids in maternal plasma for non-invasive prenatal diagnosis of monogenic diseases, placental insufficiency-related complications and Down syndrome. Thesis from Charles University in Prague. 2011. 104 pages.
Wangkumhang et al., WASP: a Web-based Allele-Specific PCR assay designing tool for detecting SNPs and mutations. BMC Genomics. Aug. 14, 2007;8:275.
Wilkins et al., IMP PCR primers detect single nucleotide polymorphisms for Anopheles gambiae species identification, Mopti and Savanna rDNA types, and resistance to dieldrin in Anopheles arabiensis. Malar J. Dec. 19, 2006;5:125.
Yi et al., PCR/LDR/capillary electrophoresis for detection of single-nucleotide differences between fetal and maternal DNA in maternal plasma. Prenat Diagn. Mar. 2009;29(3):217-22. doi: 10.1002/pd.2072.
Zhang et al., A novel multiplex tetra-primer ARMS-PCR for the simultaneous genotyping of six single nucleotide polymorphisms associated with female cancers. PLoS One. Apr. 17, 2013;8(4):e62126. doi: 10.1371/journal.pone.0062126. Print 2013.
Agbor-Enoh et al., Applying rigor and reproducibility standards to assay donor-derived cell-free DNA as a non-invasive method for detection of acute rejection and graft injury after heart transplantation. J Heart Lung Transplant. Sep. 2017;36(9):1004-1012. doi: 10.1016/j.healun.2017.05.026. Epub May 20, 2017.
Ahmed et al., Cell Free DNA and Procalcitonin as Early Markers of Complications in ICU Patients with Multiple Trauma and Major Surgery. Clin Lab. Dec. 1, 2016;62(12):2395-2404. doi: 10.7754/Clin.Lab.2016.160615.
Alachkar, Serum and urinary biomarkers in acute kidney transplant rejection. Nephrol Ther. Feb. 2012;8(1):13-9. doi: 10.1016/j.nephro.2011.07.409. Epub Oct. 21, 2011.
Almeida et al., Evaluation of 16 SNPs allele-specific to quantify post hSCT chimerism by SYBR green-based qRT-PCR. J Clin Pathol. Mar. 2013;66(3):238-42. doi: 10.1136/jclinpath-2012-201224. Epub Jan. 2, 2013.
Arshad et al., Elevated Cell-Free Mitochondrial DNA in Filtered Plasma is Associated With HIV Infection and Inflammation. J Acquir Immune Defic Syndr. May 1, 2018;78(1):111-118. doi: 10.1097/QAI.0000000000001650.
Avriel et al., Admission cell free DNA levels predict 28-day mortality in patients with severe sepsis in intensive care. PLoS One. Jun. 23, 2014;9(6):e100514. doi: 10.1371/journal.pone.0100514. eCollection 2014.
Bezieau et al., High incidence of N and K-Ras activating mutations in multiple myeloma and primary plasma cell leukemia at diagnosis. Hum Mutat. Sep. 2001;18(3):212-24. doi: 10.1002/humu.1177.
Braun et al., Limitation of Circulating cfDNA Under the Use of a Cytokine Elimination Adsorber (CytoSorb) in Cardiac Surgery. The Thoracic and Cardiovascular Surgeon. Jan. 2018; 66(S01):S1-S110.
Bronkhorst et al., The Emerging Role of Cell-Free DNA as a Molecular Marker for Cancer Management. Biomol Detect Quantif. Mar. 18, 2019;17:100087. DOI: 10.1016/J.BDQ.2019.100087. Ecollection Mar. 2019.
Cabel et al., Circulating tumor DNA changes for early monitoring of anti-PDl immunotherapy: a proof-of-concept study. Ann Oncol. Aug. 1, 2017;28(8):1996-2001. doi: 10.1093/annonc/mdx212.
Clementi et al., The Role of Cell-Free Plasma DNA in Critically Ill Patients with Sepsis. Blood Purif. 2016;41(1-3):34-40. doi: 10.1159/000440975. Epub Oct. 20, 2015.
De Vlaminck et al., Circulating cell-free DNA enables noninvasive diagnosis of heart transplant rejection. Sci Transl Med. Jun. 18, 2014;6(241):241ra77. Supplemental Materials.
De Vlaminck et al., Noninvasive monitoring of infection and rejection after lung transplantation. Proc Natl Acad Sci U S A. Oct. 27, 2015; 112(43):13336-41. doi: 10.1073/pnas.1517494112. Epub Oct. 12, 2015.
Delgado et al., Characterization of cell-free circulating DNA in plasma in patients with prostate cancer. Tumour Biol. Apr. 2013;34(2):983-6. doi: 10.1007/s13277-012-0634-6. Epub Dec. 27, 2012.
Dwivedi et al., Prognostic utility and characterization of cell-free DNA in patients with severe sepsis. Crit Care. Aug. 13, 2012;16(4):R151. doi: 10.1186/cc11466.

(56) References Cited

OTHER PUBLICATIONS

Garnacho-Montero et al., Prognostic and diagnostic value of eosinopenia, C-reactive protein, procalcitonin, and circulating cell-free DNA in critically ill patients admitted with suspicion of sepsis. Crit Care. Jun. 5, 2014;18(3):R116. doi: 10.1186/cc13908.

Gielis et al., Cell-Free DNA: An Upcoming Biomarker in Transplantation. Am J Transplant. Oct. 2015;15(10):2541-51. doi: 10.1111/ajt.13387. Epub Jul. 16, 2015.

Hasi et al., Acetaldehyde dehydrogenase 2 SNP rs671 and susceptibility to essential hypertension in Mongolians: a case control study. Genet Mol Res. Mar. 29, 2011;10(1):537-43. doi: 10.4238/vol10-1gmr1056.

Hudecova, Digital PCR analysis of circulating nucleic acids. Clin Biochem. Oct. 2015;48(15):948-56. doi: 10.1016/j.clinbiochem.2015.03.015. Epub Mar. 28, 2015.

Hugon et al., Influence of intention to adhere, beliefs and satisfaction about medicines on adherence in solid organ transplant recipients. Transplantation. Jul. 27, 2014;98(2):222-8. doi: 10.1097/TP.0000000000000221.

Jung et al., Cell-free DNA in the blood as a solid tumor biomarker—a critical appraisal of the literature. Clin Chim Acta. Nov. 11, 2010;411(21-22):1611-24. doi: 10.1016/j.cca.2010.07.032. Epub Aug. 2, 2010.

Kustanovich et al., Life and death of circulating cell-free DNA. Cancer Biol Ther. 2019;20(8):1057-1067. doi: 10.1080/15384047.2019.1598759. Epub Apr. 16, 2019.

Liu et al., ABO chimerism determined by real-time polymerase chain reaction analysis after ABO-incompatible haematopoietic stem cell transplantation. Blood Tranfus. Jan. 2013;11(1):43-52. doi: 10.2450/2012.0013-12. Epub Jul. 4, 2012.

Luo et al., Detection of usual and atypical aldehyde dehydrogenase alleles by mismatch amplification mutation assay. Clin Chem Lab Med. Dec. 2001;39(12):1195-7. doi: 10.1515/CCLM.2001.189.

Martinez-Herrero et al., Cancer protection elicited by a single nucleotide polymorphism close to the adrenomedullin gene. J Clin Endocrinol Metab. Apr. 2013;98(4):E807-10. doi: 10.1210/jc.2012-4193. Epub Feb. 28, 2013.

Purhonen et al., Human plasma cell-free DNA as a predictor of infectious complications of neutropenic fever in hematological patients. Infect Dis (Lond). Apr. 2015;47(4):255-9. doi: 10.3109/00365548.2014.985711. Epub Feb. 9, 2015.

Qin et al., Quantitative assessment of hematopoietic chimerism by quantitative real-time polymerase chain reaction of sequence polymorphism systems after hematopoietic stem cell transplantation. Chin Med J (Engl). Aug. 2011;124(15):2301-8.

Schwarzenbach et al., Cell-free nucleic acids as biomarkers in cancer patients. Nat Rev Cancer. Jun. 2011;ll(6):426-37. doi: 10.1038/nrc3066. Epub May 12, 2011.

Shimabukuro-Vornhagen et al., Cytokine release syndrome. J Immunother Cancer. Jun. 15, 2018;6(1):56. doi: 10.1186/s40425-018-0343-9.

Spindler et al., Cell-free DNA in healthy individuals, noncancerous disease and strong prognostic value in colorectal cancer. Int J Cancer. Dec. 15, 2014;135(12):2984-91. doi: 10.1002/ijc.28946. Epub Jun. 17, 2014.

Taira et al., Novel high-speed droplet-allele specific-polymerase chain reaction: application in the rapid genotyping of single nucleotide polymorphisms. Clin Chim Acta. Sep. 23, 2013;424:39-46. doi: 10.1016/j.cca.2013.04.024. Epub May 17, 2013.

[No Author Listed], ClinicalTrials.gov Identifier: NCT02109575. Quantitative Detection of Circulating Donor-Specific DNA in Organ Transplant Recipients (DTRT-Multi-Center Study) (DTRT). Apr. 10, 2014. Last updated Mar. 26, 2021. 9 pages.

[No Author Listed], HumanOmni 1 array product information datasheet. 2009. 1 page.

[No Author Listed], HumanOmni2.5-8 array product information datasheet. 2011. 1 page.

Castells et al., K-ras mutations in DNA extracted from the plasma of patients with pancreatic carcinoma: diagnostic utility and prognostic significance. J Clin Oncol. Feb. 1999;17(2):578-84. doi: 10.1200/JCO.1999.17.2.578.

Chen et al., Non-invasive prenatal diagnosis using fetal DNA in maternal plasma: a preliminary study for identification of paternally-inherited alleles using single nucleotide polymorphisms.BMJ Open. Jul. 22, 2015;5(7):e007648. doi: 10.1136/bmjopen-2015-007648.

Fleischhacker et al., Circulating nucleic acids (CNAs) and cancer—a survey. Biochim Biophys Acta. Jan. 2007;1775(1):181-232. doi: 10.1016/j.bbcan.2006.10.001. Epub Oct. 7, 2006.

Gormally et al., Amount of DNA in plasma and cancer risk: a prospective study. Int J Cancer. Sep. 20, 2004;111(5):746-9. doi: 10.1002/ijc.20327.

Karapetis et al., K-ras mutations and benefit from cetuximab in advanced colorectal cancer. N Engl J Med. Oct. 23, 2008;359(17):1757-65. doi: 10.1056/NEJMoa0804385.

Laurent-Puig et al., Clinical relevance of KRAS-mutated subclones detected with picodroplet digital PCR in advanced colorectal cancer treated with anti-EGFR therapy. Clin Cancer Res. Mar. 1, 2015;21(5):1087-97. doi: 10.1158/1078-0432.CCR-14-0983. Epub Sep. 23, 2014.

Lecomte et al., Detection of free-circulating tumor-associated DNA in plasma of colorectal cancer patients and its association with prognosis. Int J Cancer. Aug. 10, 2002;100(5):542-8. doi: 10.1002/ijc.10526.

Lievre et al., KRAS mutations as an independent prognostic factor in patients with advanced colorectal cancer treated with cetuximab. J Clin Oncol. Jan. 20, 2008;26(3):374-9. doi: 10.1200/JCO.2007.12.5906.

Misale et al., Emergence of KRAS mutations and acquired resistance to anti-EGFR therapy in colorectal cancer. Nature. Jun. 28, 2012;486(7404):532-6. doi: 10.1038/nature11156.

Mouliere et al., Circulating Cell-Free DNA from Colorectal Cancer Patients May Reveal High KRAS or BRAF Mutation Load. Transl Oncol. Jun. 1, 2013;6(3):319-28. doi: 10.1593/tlo.12445. Print Jun. 2013.

Orou et al., Allele-specific competitive blocker PCR: a one-step method with applicability to pool screening. Hum Mutat. 1995;6(2):163-9. doi: 10.1002/humu.1380060209.

Peng et al., Comparison of K-ras mutations in lung, colorectal and gastric cancer. Oncol Lett. Aug. 2014;8(2):561-565. doi: 10.3892/ol.2014.2205. Epub May 30, 2014.

Sanmamed et al., Quantitative cell-free circulating BRAFV600E mutation analysis by use of droplet digital PCR in the follow-up of patients with melanoma being treated with BRAF inhibitors. Clin Chem. Jan. 2015;61(1):297-304. doi: 10.1373/clinchem.2014.230235. Epub Nov. 19, 2014.

Sapio et al., Detection of BRAF mutation in thyroid papillary carcinomas by mutant allele-specific PCR amplification (MASA). Eur J Endocrinol. Feb. 2006;154(2):341-8. doi: 10.1530/eje.1.02072.

Schütz et al., Graft-derived cell-free DNA, a noninvasive early rejection and graft damage marker in liver transplantation: A prospective, observational, multicenter cohort study. PLoS Med. Apr. 25, 2017;14(4):e1002286. doi: 10.1371/journal.pmed.1002286. eCollection Apr. 2017.

Sefrioui et al., Clinical value of chip-based digital-PCR platform for the detection of circulating DNA in metastatic colorectal cancer. Dig Liver Dis. Oct. 2015;47(10):884-90. doi: 10.1016/j.dld.2015.05.023. Epub Jun. 5, 2015.

Spindler et al., KRAS-mutated plasma DNA as predictor of outcome from irinotecan monotherapy in metastatic colorectal cancer. Br J Cancer. Dec. 10, 2013;109(12):3067-72. doi: 10.1038/bjc.2013.633. Epub Nov. 21, 2013.

Spindler et al., Quantitative cell-free DNA, KRAS, and BRAF mutations in plasma from patients with metastatic colorectal cancer during treatment with cetuximab and irinotecan. Clin Cancer Res. Feb. 15, 2012;18(4):1177-85. doi: 10.1158/1078-0432.CCR-11-0564. Epub Jan. 6, 2012.

Tabernero et al., Analysis of circulating DNA and protein biomarkers to predict the clinical activity of regorafenib and assess prognosis in patients with metastatic colorectal cancer: a retrospective, exploratory analysis of the CORRECT trial. Lancet Oncol. Aug. 2015;16(8):937-48. doi: 10.1016/S1470-2045(15)00138-2. Epub Jul. 13, 2015.

(56) References Cited

OTHER PUBLICATIONS

Taly et al., Multiplex picodroplet digital PCR to detect KRAS mutations in circulating DNA from the plasma of colorectal cancer patients. Clin Chem. Dec. 2013;59(12):1722-31. doi: 10.1373/clinchem.2013.206359. Epub Aug. 12, 2013.

Thierry, A Targeted Q-PCR-Based Method for Point Mutation Testing by Analyzing Circulating DNA for Cancer Management Care. Methods Mol Biol. 2016;1392:1-16. doi: 10.1007/978-1-4939-3360-0_1.

Yamada et al., Detection of K-ras gene mutations in plasma DNA of patients with pancreatic adenocarcinoma: correlation with clinicopathological features. Clin Cancer Res. Jun. 1998;4(6):1527-32.

Agbor-Enoh et al., Cell-Free DNA to Detect Heart Allograft Acute Rejection. Circulation. Mar. 23, 2021;143(12):1184-1197. doi: 10.1161/CIRCULATIONAHA.120.049098. Epub Jan. 13, 2021.

Andargie et al., Cell-free DNA maps COVID-19 tissue injury and risk of death and can cause tissue injury. JCI Insight. Apr. 8, 2021;6(7):e147610. doi: 10.1172/jci.insight.147610.

Bienkowski et al., Liquid biopsy for minimally invasive heart transplant monitoring: a pilot study. J Clin Pathol. Aug. 2020;73(8):507-510. doi: 10.1136/jclinpath-2019-205926. Epub Dec. 5, 2019.

Cagliani et al., Deoxyribonuclease Reduces Tissue Injury and Improves Survival After Hemorrhagic Shock. J Surg Res. May 2020;249:104-113. doi: 10.1016/j.jss.2019.11.036. Epub Jan. 8, 2020.

Chan et al., Bioinformatics analysis of circulating cell-free DNA sequencing data. Clin Biochem. Oct. 2015;48(15):962-75. doi: 10.1016/j.clinbiochem.2015.04.022. Epub May 9, 2015.

Cheng et al., Cell-Free DNA in Blood Reveals Significant Cell, Tissue and Organ Specific injury and Predicts COVID-19 Severity. medRxiv. Jul. 29, 2020;2020.07.27.20163188. doi: 10.1101/2020.07.27.20163188. Preprint.

Dandel et al., Nonvasive cardiac allograft rejection surveillance: reliability and clinical value for prevention of heart failure. Heart Fail Rev. Mar. 2021;26(2):319-336. doi: 10.1007/s10741-020-10023-3. Epub Sep. 5, 2020.

Deshpande et al., Relationship Between Donor Fraction Cell-Free DNA and Treatment for Rejection in Heart Transplantation. Pediatric Transplantation. Jun. 2022; 26(4):e14264. https://doi.org/10.1111/petr.14264.

Ding et al., New Progress in Plasma Cell-free DNA in Clinical Applications. Progress in Modern Biomedicine. 2016; 18: 3593-3596, 3476.

Huang et al., Circulating cell-free DNA levels correlate with postresuscitation survival rates in out-of-hospital cardiac arrest patients. Resuscitation. Feb. 2012;83(2):213-8. doi: 10.1016/j.resuscitation.2011.07.039. Epub Aug. 22, 2011.

Jing et al., Cell-free DNA: characteristics, detection and its applications in myocardial infarction. Curr Pharm Des. 2013;19(28):5135-45. doi: 10.2174/13816128113199280012.

Khush et al., Noninvasive detection of graft injury after heart transplant using donor/\derived cell/\free DNA: A prospective multicenter study. Am J Transplant. Oct. 2019;19(10):2889-2899. doi: 10.1111/ajt.15339. Epub Apr. 8, 2019.

Kirkizlar et al., Detection of Clonal and Subclonal Copy-Number Variants in Cell-Free DNA from Patients with Breast Cancer Using a Massively Multiplexed PCR Methodology. Transl Oncol. Oct. 2015;8(5):407-416. doi: 10.1016/j.tranon.2015.08.004.

Liang et al., Cationic nanoparticle as an inhibitor of cell-free DNA-induced inflammation. Nat Commun. Oct. 16, 2018;9(1):4291. doi: 10.1038/s41467-018-06603-5.

Mengel et al., The molecular phenotype of heart transplant biopsies: relationship to histopathological and clinical variables. Am J Transplant. Sep. 2010;10(9):2105-15. doi: 10.1111/j.1600-6143.2010.03182.x.

North et al., Cell-free DNA donor fraction analysis in pediatric and adult heart transplant patients by multiplexed allele-specific quantitative PCR: Validation of a rapid and highly sensitive clinical test for stratification of rejection probability. PLoS One. Jan. 13, 2020;15(1):e0227385. doi: 10.1371/journal.pone.0227385. eCollection 2020.

Peyster et al., Advanced Morphologic Analysis for Diagnosing Allograft Rejection: The Case of Cardiac Transplant Rejection. Transplantation. Aug. 2018;102(8):1230-1239. doi: 10.1097/TP.0000000000002189.

Richmond et al., Donor fraction cell-free DNA and rejection in adult and pediatric heart transplantation. J Heart Lung Transplant. May 2020;39(5):454-463. doi: 10.1016/j.healun.2019.11.015. Epub Nov. 29, 2019.

Scott et al., Elevated nuclear and mitochondrial cell-free deoxyribonucleic acid measurements are associated with death after infant cardiac surgery. J Thorac Cardiovasc Surg. Aug. 2022;164(2):367-375. doi: 10.1016/j.jtcvs.2021.10.066. Epub Dec. 24, 2021.

Scott et al., Total Cell-Free DNA Predicts Death and Infection Following Pediatric and Adult Heart Transplantation. Ann Thorac Surg. Oct. 2021;112(4):1282-1289. doi: 10.1016/j.athoracsur.2020.08.006. Epub Oct. 8, 2020.

Tanem et al., Abstract 16873: Association of Preoperative Cell-Free DNA Levels and Outcome Following Pediatric Cardiopulmonary Bypass. Circulation. Nov. 17, 2020; 142(S3): 1-6. https://doi.org/10.1161/circ.142.suppl_3.16873.

Wapner et al., Expanding the scope of noninvasive prenatal testing: detection of fetal microdeletion syndromes. Am J Obstet Gynecol. Mar. 2015;212(3):332.e1-9. doi: 10.1016/j.ajog.2014.11.041. Epub Dec. 2, 2014.

Zangwill et al., Effect of endomyocardial biopsy on levels of donor-specific cell-free DNA. J Heart Lung Transplant. Oct. 2019;38(10):1118-1120. doi: 10.1016/j.healun.2019.06.005. Epub Jun. 28, 2019.

Akobeng, Understanding diagnostic tests 3: Receiver operating characteristic curves. Acta Paediatr. May 2007:96(5):644-7. doi: 10.1111/j.1651-2227.2006.00178.x. Epub Mar. 21, 2007.

Toshokan, Q & A. J-STAGE. Dec. 2004; 51(4): 387-388. Released on J-STAGE: Sep. 21, 2011. https://doi.org/10.7142/igakutoshokan.51.387 [last accessed Aug. 8, 2023].

1. Infection(y) – Total cfDNA (all 298 samples)

All 298 are used

-2.9484 +0.0146 * TotalcdDNA  (p<0.0001)

AUC = 0.7006

Sensitivity = 0.636

Specificity = 0.833

Cutoff = 21.18

Arrest – Total cfDNA (1 sample per subject – n=88)

Last sample from all (N=88)

-2.6123 + 0.0101 * Total cfDNA  (p=0.05)

AUC = 0.8578
sensitivity ~ 1
specificity = 0.712
Cut= 8.18

|  | Death | | p-value |
|---|---|---|---|
| | No | Yes | |
| Total cfDNA | | | |
| N | 77 | 8 | |
| median [IQR] | 4.98 [3.70, 8.19] | 75.56 [14.84, 204.98] | <0.001 |
| OR (95% CI) per doubling * | 3.17 (1.71, 5.91) | | <0.001 |
| *odds ratio of alive versus dead per doubling of cfDNA | | | |

| Reference Variable | Death | |
|---|---|---|
| Classification variable: | Total cfDNA | |
| Empirical optimal cutpoint(95% CI) | 8.62 (3.48, 21.38) | p<0.001 |
| Sensitivity at cutpoint: | 1.00 | |
| Specificity at cutpoint: | 0.79 | |
| Area under the ROC curve at cutpoint | 0.90 | |
| PPV | 33.3% (24.4, 43.6) | |
| NPV | 100% | |

Fig. 15

|  | Cardiac Arrest | | |
| --- | --- | --- | --- |
|  | No | Yes | p-value |
| Total cfDNA | | | |
| N | 77 | 5 | |
| median [IQR] | 5.00 [3.78, 8.51] | 9.51 [9.03, 20.96] | 0.012 |
| OR (95% CI) per doubling * | 1.61 (0.99, 2.63) | | 0.056 |
| *odds ratio of alive versus dead per doubling of cfDNA | | | |

|  | Cardiac Arrest | |
| --- | --- | --- |
| Reference Variable | | |
| Classification variable: | Total cfDNA | |
| Empirical optimal cutpoint (95% CI) | 8.17 (5.21, 12.81) | p<0.001 |
| Sensitivity at cutpoint: | 1.00 | |
| Specificity at cutpoint: | 0.73 | |
| Area under the ROC curve at cutpoint | 0.86 | |
| PPV | 19.2% (14.2, 25.5) | |
| NPV | 100% | |

Fig. 17

| | Treatment for Infection at Draw | | Null Hypothesis | Statistical Test |
|---|---|---|---|---|
| | No | Yes | The medians are the same across treatment for infection | |
| | median [IQR] | median [IQR] | | |
| N | 273 | 19 | | |
| Total cfDNA | 7.67 [4.29, 15.94] | 21.97 [4.98, 166.07] | p=0.343 | Independent samples median test |
| Cutpoint estimation | | | | |
| Reference Variable | Infection | | | |
| Classification variable: | Total cfDNA | | | |
| Empirical optimal cutpoint(95% CI) | 21.44 (10.17, 45.18) | | p<0.001 | |
| Sensitivity at cutpoint | 0.58 | | | |
| Specificity at cutpoint | 0.85 | | | |
| Area under the ROC curve at cutpoint | 0.71 | | | |
| PPV | 21.2% (14.3, 30.2) | | | |
| NPV | 96.7% (94.5, 98.0) | | | |

Fig. 19 ial Application No. 62/572,556, filed Oct. 15, 2017, the
ASSESSING TRANSPLANT COMPLICATION RISK WITH TOTAL CELL-FREE DNA

RELATED APPLICATIONS

This application is a national stage filing under 35 U.S.C. § 371 of international PCT application, PCT/US2018/038598, filed Jun. 20, 2018, which claims the benefit of priority under 35 U.S.C. § 119 to U.S. Provisional Application No. 62/522,533, filed Jun. 20, 2017 and U.S. Provisional Application No. 62/572,556, filed Oct. 15, 2017, the entire contents of each of which are incorporated herein by reference.

FIELD OF THE INVENTION

This invention relates to methods and compositions for assessing an amount of total cell-free nucleic acids in a sample from a transplant subject. Such amounts can be used to determine risk of one or more complications associated with transplantation. This invention further relates to methods and compositions for assessing the amount of total cell-free deoxyribonucleic acid (cf-DNA) using assays such as multiplexed optimized mismatch amplification (MOMA) and/or sequencing techniques for the assessment of the risk of transplant complications.

SUMMARY OF INVENTION

The present disclosure is based, at least in part on the surprising discovery that risk of complications following transplantation, such as organ transplantation, is correlated with the amount of total cell-free DNA. Using any one of a variety of means to quantify total cell-free DNA in a sample, the risk of transplant complications, including infection, cardiac arrest, and death can be determined as well as monitored over time.

Provided herein are methods, compositions and kits related to such a determination. The methods, compositions, or kits can be any one of the methods, compositions, or kits, respectively, provided herein, including any one of those of the Examples or Figures.

In one embodiment of any one of the methods provided, the method further comprises obtaining a sample from the subject.

In one embodiment, any one of the embodiments for the methods provided herein can be an embodiment for any one of the compositions, kits or reports provided. In one embodiment, any one of the embodiments for the compositions, kits or reports provided herein can be an embodiment for any one of the methods provided herein.

In one aspect, a report or database comprising one or more of the amounts provided herein is provided.

In one aspect, any one of the methods provided herein is provided. In one embodiment of any one of the methods provided herein, the amount indicative of a specific risk or complication is any one of the cutpoints or ranges thereof described herein. In one embodiment of any one of the methods provided herein, the time for obtaining the sample is any one of the times described herein. In one embodiment of any one of the methods provided herein, the subject is any one of the subjects described herein.

In one aspect, a method of treating a subject, determining a treatment regimen for a subject or providing information about a treatment to the subject, based on the amount of total cell-free DNA or any one of the methods of analysis provided herein is provided. In one embodiment of any one of such methods, the method comprises a step of treating the subject or providing information about a treatment to the subject. In one embodiment of any one of the methods of treating, the treatment may be any one of the treatments provided herein. In one embodiment of any one of the methods of treating, the treatment is for any one of the conditions provided herein. Examples of which are provided herein or otherwise known to those of ordinary skill in the art.

In one aspect, any one of the methods provided herein may be a method of treating a transplant subject, such as a cardiac transplant subject.

BRIEF DESCRIPTION OF FIGURES

The accompanying figures are not intended to be drawn to scale. The figures are illustrative only and are not required for enablement of the disclosure.

FIG. 15 is a table showing the experimental determination of a cutpoint (threshold) for death using total cf-DNA from 85 samples.

FIG. 17 is a table showing the experimental determination of a cutpoint (threshold) for cardiac arrest using total cf-DNA from 85 samples.

FIG. 19 is a table showing the experimental determination of a cutpoint (threshold) for infection (i.e., whether the subject was undergoing treatment for infection at the time of the sample) using total cf-DNA from 292 samples.

DETAILED DESCRIPTION OF THE INVENTION

Figure 1:
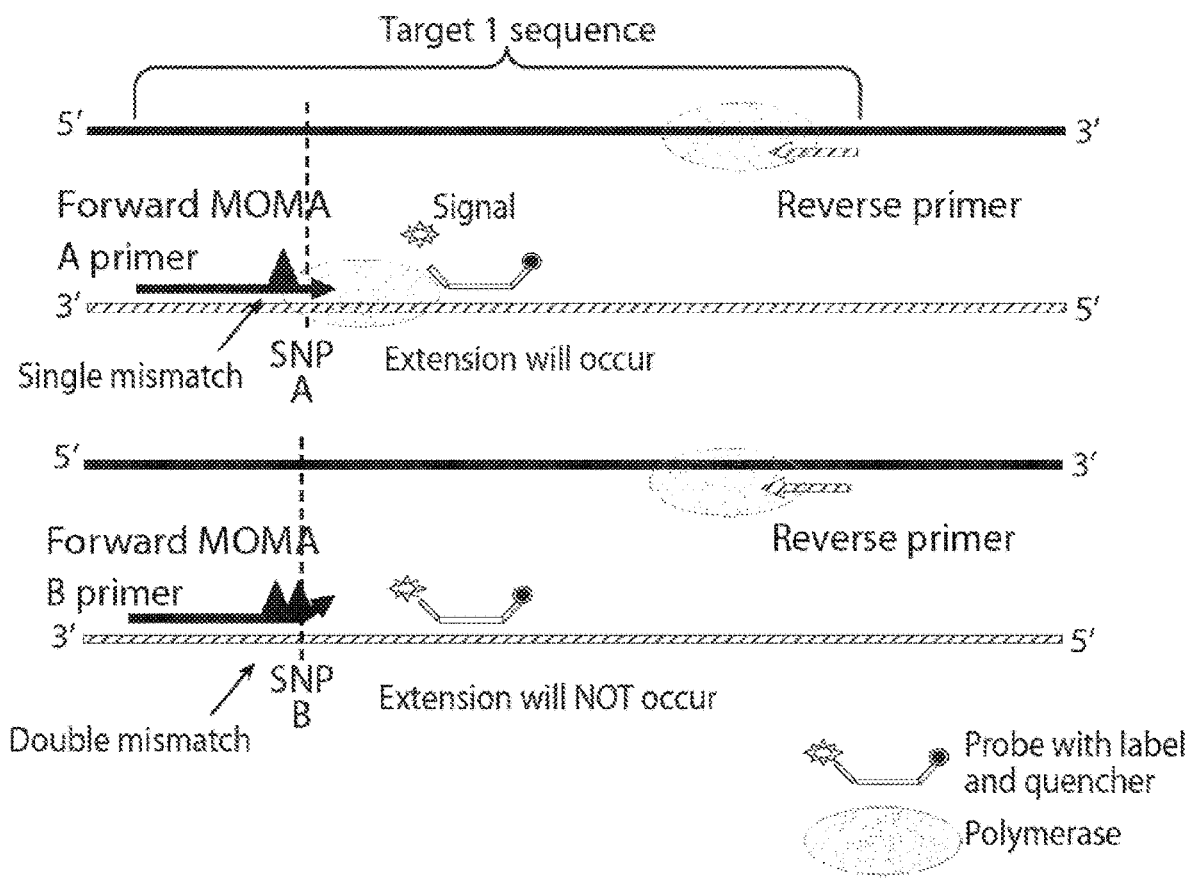
FIG. 1 provides an exemplary, non-limiting diagram of MOMA primers. In a polymerase chain reaction (PCR) assay, extension of the sequence containing SNV A is expected to occur, resulting in the detection of SNV A, which may be subsequently quantified. Extension of the SNV B; however, is not expected to occur due to the double mismatch.

It has been found that total cell-free DNA (total cf-DNA) is correlated with transplant complications and can be used to assess and/or monitor a subject as a result. Complications include, but are not limited to, infection, cardiac arrest, and/or death. Therefore, aspects of the disclosure relate, at least in part, to methods of quantifying total cf-DNA in a sample in order to assess or determine a transplant complication or risk associated therewith. In some embodiments, the subject may be on mechanical support (e.g., a ventilator) and can be monitored with any one of the methods provided herein.

As used herein, "cell-free DNA" (or "cf-DNA") is DNA that is present outside of a cell, e.g., in the blood, plasma, serum, urine, etc. of a subject. Without wishing to be bound by any particular theory or mechanism, it is believed that cf-DNA is released from cells, e.g., via apoptosis of the cells. "Total cell-free DNA" (or "total cf-DNA") is the amount of cf-DNA present in a sample, and can include both donor and recipient cf-DNA when assessing a sample from a transplant recipient. As used herein, the compositions and methods provided herein can be used to determine an amount of total cell-free DNA and a subject's risk of complications associated with a transplant.

Provided herein are methods and compositions that can be used to measure total cf-DNA, which may then be used to assess the subject's risk of complications associated with a transplant. As used herein, "transplant" refers to the moving of an organ or tissue from a donor to a recipient for the purpose of replacing the recipient's damaged or absent organ or tissue. Any one of the methods or compositions provided herein may be used on a sample from a subject that has undergone a transplant of an organ or tissue. In some embodiments, the transplant is a heart transplant.

Importantly, amounts of total cf-DNA can be used to assess or determine a risk of a transplant complication. Transplant complications include, cardiac arrest, infection and death. As provided herein, any one of the methods can be used to assess a subject that has or is suspected of having a transplant complication. As used herein, "suspected of having" refers to a subject whereby a clinician believes there is a likelihood the subject has a specific condition, such as a transplant complication. In one embodiment of any one of the methods provided herein, the subject may be one that has a transplant complication or that a clinician believes there is a likelihood of having a transplant complication. In some embodiments, any one of the methods can be used to assess a subject that has had or is at risk of having a transplant complication. Subjects may be suspected of having, determined to have had, or determined to have a likelihood or risk of having a transplant complication based on symptoms (and/or lack thereof). However, in some embodiments, the subject is suspected of having, determined to have had, or determined to have a likelihood or risk of having a transplant complication based on one or more other tests. In such an embodiment, the methods provided herein can be used to confirm such a finding or monitor such a subject for worsening or improving condition.

A subject may be assessed by determining or obtaining one or more amounts of total cf-DNA. An amount of total cf-DNA may be determined with experimental techniques, such as those provided elsewhere herein. "Obtaining" as used herein refers to any method by which the respective information or materials can be acquired. Thus, the respective information can be acquired by experimental methods. Respective materials can be created, designed, etc. with various experimental or laboratory methods, in some embodiments. The respective information or materials can also be acquired by being given or provided with the information, such as in a report, or materials. Materials may be given or provided through commercial means (i.e. by purchasing), in some embodiments.

Because of the ability to determine amounts of nucleic acids, such as cf-DNA, and the correlation with transplant complications, the methods and compositions provided herein can be used to assess subjects. Thus, a risk of improving or worsening condition can be determined in such subjects. A "risk" as provided herein, refers to the presence or absence or progression of any undesirable condition in a subject, or an increased likelihood of the presence or absence or progression of such a condition. As provided herein "increased risk" refers to the presence or progression of any undesirable condition in a subject or an increased likelihood of the presence or progression of such a condition. As provided herein, "decreased risk" refers to the absence of any undesirable condition or progression in a subject or a decreased likelihood of the presence or progression (or increased likelihood of the absence or nonprogression) of such a condition.

As provided herein, early detection or monitoring of transplant complications can facilitate treatment and improve clinical outcomes. As mentioned above, any one of the methods provided can be performed on a subject that has or is suspected of having a transplant complication. Such methods can be used to monitor a subject over time, with or without treatment. Further, such methods can aid in the selection, administration and/or monitoring of a treatment or therapy. Accordingly, the methods provided herein can be used to determine a treatment or monitoring regimen. The subject may be any one of the subjects provided herein. In one embodiment of any one of the methods provided herein, the subject is one that is on mechanical support or that is in need of mechanical support.

"Determining a treatment regimen", as used herein, refers to the determination of a course of action for treatment of the subject. In one embodiment of any one of the methods provided herein, determining a treatment regimen includes determining an appropriate therapy or information regarding an appropriate therapy to provide to a subject. In some embodiments of any one of the methods provided herein, the determining includes providing an appropriate therapy or information regarding an appropriate therapy to a subject. As used herein, information regarding a treatment or therapy or monitoring may be provided in written form or electronic form. In some embodiments, the information may be provided as computer-readable instructions. In some embodiments, the information may be provided orally.

Treatments include any treatment that is indicated based on the complication risk that is determined. In one embodiment, the treatment is a cardiac arrest treatment. Cardiac arrest treatments include, for example, blood pressure medications, involuntary nervous system blockers, and anti-arrhythmic agents. Further, a subject may be treated with coronary catheterization and/or a cardioverter-defibrillator may be implanted.

In another embodiment, the treatment can be a treatment for infection. In some embodiments, therapies for treating infection include therapies for treating a bacterial, fungal and/or viral infection. Such therapies include antibiotics. Other examples include, but are not limited to, amebicides, aminoglycosides, anthelmintics, antifungals, azole antifungals, echinocandins, polyenes, diarylquinolines, hydrazide derivatives, nicotinic acid derivatives, rifamycin derivatives, streptomyces derivatives, antiviral agents, chemokine receptor antagonist, integrase strand transfer inhibitor, neuraminidase inhibitors, NNRTIs, NS5A inhibitors, nucleoside reverse transcriptase inhibitors (NRTIs), protease inhibitors, purine nucleosides, carbapenems, cephalosporins, glycylcyclines, leprostatics, lincomycin derivatives, macrolide derivatives, ketolides, macrolides, oxazolidinone antibiotics, penicillins, beta-lactamase inhibitors, quinolones, sulfonamides, and tetracyclines.

Anti-rejection therapies include, for example, immunosuppressives. Immunosuppressives include, but are not limited to, corticosteroids (e.g., prednisolone or hydrocortisone), glucocorticoids, cytostatics, alkylating agents (e.g., nitrogen mustards (cyclophosphamide), nitrosoureas, platinum compounds, cyclophosphamide (Cytoxan)), antimetabolites (e.g., folic acid analogues, such as methotrexate, purine analogues, such as azathioprine and mercaptopurine, pyrimidine analogues, and protein synthesis inhibitors), cytotoxic antibiotics (e.g., dactinomycin, anthracyclines, mitomycin C, bleomycin, mithramycin), antibodies (e.g., anti-CD20, anti-IL-1, anti-IL-2Ralpha, anti-T-cell or anti-CD-3 monoclonals and polyclonals, such as Atgam, and Thymoglobuline), drugs acting on immunophilins, ciclosporin, tacrolimus, sirolimus, interferons, opiods, TNF-binding proteins, mycophenolate, fingolimod and myriocin. In some embodiments, anti-rejection therapy comprises blood transfer or marrow transplant. Therapies can also include intravenous fluids, antibiotics, surgical drainage, early goal directed therapy (EGDT), vasopressors, steroids, activated protein C, drotrecogin alfa (activated), oxygen and appropriate support for organ dysfunction. This may include hemodialysis in kidney failure, mechanical ventilation in pulmonary dysfunction, transfusion of blood products, and drug and fluid therapy for circulatory failure. Ensuring adequate nutrition—preferably by enteral feeding, but if necessary, by parenteral nutrition—can also be included particularly during prolonged illness. Other associated therapies can include insulin and medication to prevent deep vein thrombosis and gastric ulcers. Other such therapies are known to those of ordinary skill in the art.

Other therapies are known to those of ordinary skill in the art.

Administration of a treatment or therapy may be accomplished by any method known in the art (see, e.g., Harrison's Principle of Internal Medicine, McGraw Hill Inc.). Preferably, administration of a treatment or therapy occurs in a therapeutically effective amount. Administration may be local or systemic. Administration may be parenteral (e.g., intravenous, subcutaneous, or intradermal) or oral. Compositions for different routes of administration are known in the art (see, e.g., Remington's Pharmaceutical Sciences by E. W. Martin).

The treatment and clinical course may be determined by the subject's condition as determined as provided herein and/or the subject's associated expected outcome. For example, if the amount of total cf-DNA is 8 ng/mL or greater, the subject may be treated with, or provided information related thereto, a therapy, such as those described above.

"Determining a monitoring regimen", as used herein, refers to determining a course of action to monitor a condition in the subject over time. In one embodiment of any one of the methods provided herein, determining a monitoring regimen includes determining an appropriate course of action for determining the amount of total cf-DNA in the subject over time or at a subsequent point in time, or suggesting such monitoring to the subject. This can allow for the measurement of variations in a clinical state and/or permit calculation of normal values or baseline levels (as well as comparisons thereto). In some embodiments of any one of the methods provided herein determining a monitoring regimen includes determining the timing and/or frequency of obtaining samples from the subject and/or determining or obtaining an amount of total cf-DNA.

In some embodiments of any one of the methods provided herein, the total cf-DNA may be detected as soon as 4 days after transplant surgery. In other embodiments, the total cf-DNA may be quantified within 5, 6, 7 or 8 or more days after transplant. In order to monitor the subject's total cf-DNA levels, samples may be taken at monthly, bimonthly, or at more frequent intervals for up to 6 months, up to 8 months, up to 10 months, up to 12 months, or longer. As increasing levels of total cf-DNA have been found to correlate with increased risk, a clinician may determine that a subject should undergo more frequent sampling if the subject's total cf-DNA is found to increase between time points. If a subject is found to have decreasing levels of total cf-DNA between time points, a clinician may determine that less frequent sampling is sufficient. Timing and/or frequency of monitoring may also be determined by a comparison to one or more threshold values. For example, if the amount of total cf-DNA is equal to or greater than 8 ng/mL (or any one of the thresholds provided herein) and/or is increasing, more frequent sampling may be needed, whereas, if the amount of total cf-DNA is less than 8 ng/mL (or any one of the thresholds provided herein), and/or is not increasing, less frequent sampling may be required. Generally, subjects with higher or increasing amounts of total cf-DNA require closer monitoring and more frequent sampling. In some embodiments of any one of the methods provided herein, each amount and time point may be recorded in a report or in a database.

Reports with any one or more of the values as provided herein are also provided in an aspect. Reports may be in oral, written (or hard copy) or electronic form, such as in a form that can be visualized or displayed. Preferably, the report provides the amount of total nucleic acids, such as total cf-DNA, in a sample. In some embodiments, the report provides amounts of total nucleic acids, such as total cf-DNA, in samples from a subject over time.

In some embodiments, the amounts are in or entered into a database. In one aspect, a database with such values is provided. From the amount(s), a clinician may assess the need for a treatment or monitoring of a subject. Accordingly, in any one of the methods provided herein, the method can include assessing the amount of nucleic acids in the subject at more than one point in time. Such assessing can be performed with any one of the methods or compositions provided herein.

As used herein, "amount" refers to any quantitative value for the measurement of nucleic acids and can be given in an absolute or relative amount. Further, the amount can be a total amount, frequency, ratio, percentage, etc. As used herein, the term "level" can be used instead of "amount" but is intended to refer to the same types of values. Generally, unless otherwise provided, the amounts provided herein represent the total cf-DNA in a sample.

In some embodiments, any one of the methods provided herein can comprise comparing an amount of total nucleic acids to a threshold value, or to one or more prior amounts, to identify a subject at increased or decreased risk. In some embodiments of any one of the methods provided herein, a subject having an increased amount of total nucleic acids compared to a threshold value, or to one or more prior amounts, is identified as being at increased risk. In some embodiments of any one of the methods provided herein, a subject having a decreased or similar amount of total nucleic acids compared to a threshold value, or to one or more prior amounts, is identified as being at decreased or not increased risk.

"Threshold" or "threshold value" or "cutpoint", as used herein, refers to any predetermined level or range of levels that is indicative of the presence or absence of a condition or the presence or absence of a risk. The threshold value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quadrants, the lowest quadrant being subjects with the lowest risk and the highest quadrant being subjects with the highest risk. The threshold value can depend upon the particular population selected. For example, an apparently healthy population will have a different 'normal' range. As another example, a threshold value can be determined from baseline values before the presence of a condition or risk or after a course of treatment. Such a baseline can be indicative of a normal or other state in the subject not correlated with the risk or condition that is being tested for. In some embodiments, the threshold value can be a baseline value of the subject being tested. Accordingly, the predetermined values selected may take into account the category in which the subject falls. Appropriate ranges and categories can be selected with no more than routine experimentation by those of ordinary skill in the art. The threshold value of any one of the methods provided herein, can be any one of the threshold values provided herein, such as in the Examples or Figures.

The threshold values provided herein can be used to determine a risk of transplant complication in a subject. Accordingly, if the amount of total cf-DNA measured is equal to or greater than 8, 9, 10, 11, 12, 13, 14, 15, 16, 17, 18, 19 or 20 ng/mL, then the subject may be determined to be at increased risk of a complication. For example, an amount equal to or greater than 8 or 9 ng/mL may be indicative of cardiac arrest. As another example, an amount equal to or greater than 20 ng/mL may be indicative of infection. The determination can be done based on any one of the comparisons as provided herein with or without other indicators of such a complication.

The threshold values can also be used for comparisons to make treatment and/or monitoring decisions. For example, if the amount of total cf-DNA is greater than one of the thresholds provided herein and/or increasing over time, further monitoring may be indicated. As a further example, if the amount is greater than any one of the thresholds provided herein, treatment of the subject may be indicated. If the amount is greater than any one of the thresholds provided herein, additional testing of the subject, such as with a biopsy may be indicated.

Accordingly, any one of the methods provided herein may further include an additional test(s) for assessing the subject, or a step of suggesting such further testing to the subject (or providing information about such further testing). The additional test(s) may be any one of the methods provided herein. The additional test(s) may be any one of the other methods provided herein or otherwise known in the art as appropriate. The type of additional test(s) will depend upon the condition of the subject and/or is well within the determination of the skilled artisan.

Exemplary additional tests for subjects suspected of infection include, but are not limited to, blood tests, urine tests, throat swabs, and spinal tap.

Exemplary additional tests for subjects, include, but are not limited to, echocardiogram, coronary angiography, intravascular ultrasound (IVUS), biopsy (e.g., endomycardial biopsy), stress echocardiography, CT coronary angiography, coronary flow reserve assessment (contrast-enhanced echocardiography), stress myocardial perfusion scintigraphy, positron emission tomography (PET) scanning, and measurement of serum biomarkers, such as BNP and/or troponin.

The amount of total cf-DNA may be determined by a number of methods. In some embodiments such a method is a sequencing-based method. For example, the total cf-DNA may be measured by analyzing the DNA of a sample to identify multiple loci, an allele of each of the loci may be determined, and informative loci may be selected based on the determined alleles. As used herein, "loci" refer to nucleotide positions in a nucleic acid, e.g., a nucleotide position on a chromosome or in a gene. As used herein, "informative loci" refers to a locus where the genotype of the subject is homozygous for the major allele, while the genotype of the donor is homozygous or heterozygous for the minor allele. As used herein, "minor allele" refers to the allele that is less frequent in the population of nucleic acids for a locus. In some embodiments, the minor allele is the nucleotide identity at the locus in the nucleic acid of the donor. A "major allele", on the other hand, refers to the more frequent allele in a population. In some embodiments, the major allele is the nucleotide identity at the locus in the nucleic acid of the subject.

In some embodiments, the informative loci and alleles can be determined based on prior genotyping of the nucleic acids of the subject and the nucleic acids of the donor. For example, the genotype of the recipient and donor can be compared, and informative loci can be identified as those loci where the recipient is homozygous for a nucleotide identity and the donor is heterozygous or homozygous for a different nucleotide identity. Methods for genotyping are well known in the art and further described herein. In this example, the minor and major allele may be identified by determining the relative quantities of each allele at the informative locus and/or may be identified as the nucleotide identity at the informative locus in the donor DNA (minor allele) and the recipient DNA (major allele). Accordingly, the methods provided can further include a step of genotyping the recipient and donor, or obtaining or being provided with such genotypes.

The DNA may be analyzed using any suitable next generation or high-throughput sequencing and/or genotyping technique. Examples of next generation and high-throughput sequencing and/or genotyping techniques include, but are not limited to, massively parallel signature sequencing, polony sequencing, 454 pyrosequencing, Illumina (Solexa) sequencing, SOLiD sequencing, ion semiconductor sequencing, DNA nanoball sequencing, heliscope single molecule sequencing, single molecule real time (SMRT) sequencing, MassARRAY®, and Digital Analysis of Selected Regions (DANSR™) (see, e.g., Stein R A (1 Sept. 2008). "Next-Generation Sequencing Update". Genetic Engineering & Biotechnology News 28 (15); Quail, Michael; Smith, Miriam E; Coupland, Paul; Otto, Thomas D; Harris, Simon R; Connor, Thomas R; Bertoni, Anna; Swerdlow, Harold P; Gu, Yong (1 Jan. 2012). "A tale of three next generation sequencing platforms: comparison of Ion torrent, pacific biosciences and illumina MiSeq sequencers". BMC Genomics 13 (1): 341; Liu, Lin; Li, Yinhu; Li, Siliang; Hu, Ni; He, Yimin; Pong, Ray; Lin, Danni; Lu, Lihua; Law, Maggie (1 Jan. 2012). "Comparison of Next-Generation Sequencing Systems". Journal of Biomedicine and Biotechnology 2012: 1-11; Qualitative and quantitative genotyping using single base primer extension coupled with matrix-assisted laser desorption/ionization time-of-flight mass spectrometry (MassARRAY®). Methods Mol Biol. 2009; 578: 307-43; Chu T, Bunce K, Hogge W A, Peters D G. A novel approach toward the challenge of accurately quantifying fetal DNA in maternal plasma. Prenat Diagn 2010; 30:1226-9; and Suzuki N, Kamataki A, Yamaki J, Homma Y. Characterization of circulating DNA in healthy human plasma. Clinica chimica acta; International Journal of Clinical Chemistry 2008; 387:55-8).

In one embodiment, any one of the methods for determining total cf-DNA may be any one of the methods of U.S. Publication No. 2015-0086477-A1, and such methods are incorporated herein by reference in their entirety.

An amount of total cf-DNA may also be determined by a MOMA assay. In one embodiment, any one of the methods for determining total cf-DNA may be any one of the methods of PCT Publication No. WO 2016/176662 A1, and such methods are incorporated herein by reference in their entirety.

The total cf-DNA may be determined for a plurality of SNV targets. A "plurality of SNV targets" refers to more than one SNV target where for each target there are at least two alleles. In some embodiments, each SNV target is biallelic and a primer pair specific to each allele of the SNV target is used to specifically amplify nucleic acids of each allele, where amplification occurs if the nucleic acid of the specific allele is present in the sample.

In an embodiment of any one of the methods or compositions provided herein, one or more primer pairs for SNV target(s) can be pre-selected based on knowledge that the SNV targets will be informative, such as with knowledge of genotype. In other embodiments of any one of the methods provided herein, the genotype of the donor is unknown. In an embodiment of such cases, the donor genotype may be inferred with an expectation maximization method. As an example, using the known recipient genotype, targets known to be homozygous in the recipient can be selected. Any contaminants can be attributed to donor-specific nucleic acids, and the resulting assay collection will consist of a tri-modal distribution: non-, half-, and fully-informative assays. With a sufficient number of recipient homozygous assays, the presence of donor fully-informative assays can be inferred.

In another embodiment of any one of the methods or compositions provided herein, primer pairs for a plurality of SNV targets can be selected for the likelihood at least one (or more) may be informative. In such embodiments, primer pairs for a panel of SNV targets are used in any one of the methods provided herein. In some embodiments, the panel of SNV targets is a panel of at least 30, 35, 40, 45, 50, 55, 60, 65, 70, 75, 80, 85, 90, 95 or more possible targets.

As used herein, "an informative SNV target" is one in which amplification with primers as provided herein occurs, and the results of which are informative. "Informative results" as provided herein are the results that can be used to quantify the level of total nucleic acids in a sample. The amount of total nucleic acids may be determined with the quantities of the major and minor alleles in some embodiments.

Primers for use in MOMA assays may be obtained, and any one of the methods provided herein can include a step of obtaining one or more primer pairs for performing the amplification-based quantification assays, such as PCR assays. Generally, the primers possess unique properties that facilitate their use in quantifying amounts of nucleic acids. For example, a forward primer of a primer pair can be mismatched at a 3' nucleotide (e.g., penultimate 3' nucleotide). In some embodiments of any one of the methods or compositions provided, this mismatch is at a 3' nucleotide but adjacent to the SNV position. In some embodiments of any one of the methods or composition provided, the mismatch positioning of the primer relative to a SNV position is as shown in FIG. 1. Generally, such a forward primer, even with the 3' mismatch, will produce an amplification product (in conjunction with a suitable reverse primer) in an amplification reaction, such as a PCR reaction, thus allowing for the amplification and resulting detection of a nucleic acid with the respective SNV. If the particular SNV is not present, and there is a double mismatch with respect to the other allele of the SNV target, an amplification product will generally not be produced. Preferably, in some embodiments of any one of the methods or compositions provided herein, for each SNV target, a primer pair is obtained whereby specific amplification of each allele can occur without amplification of the other allele(s). "Specific amplification" refers to the amplification of a specific allele of a target without substantial amplification of another nucleic acid or without amplification of another nucleic acid sequence above background or noise. In some embodiments, specific amplification results only in the amplification of the specific allele.

In some embodiments of any one of the methods or compositions provided herein, for each SNV target that is biallelic, there are two primer pairs, each specific to one of the two alleles and thus have a single mismatch with respect to the allele it is to amplify and a double mismatch with respect to the allele it is not to amplify (if nucleic acids of these alleles are present). In some embodiments of any one of the methods or compositions provided herein, the mismatch primer is the forward primer. In some embodiments of any one of the methods or compositions provided herein, the reverse primer of the two primer pairs for each SNV target is the same.

These concepts can be used in the design of primer pairs for any one of the methods and compositions provided herein. It should be appreciated that the forward and reverse primers are designed to bind opposite strands (e.g., a sense strand and an antisense strand) in order to amplify a fragment of a specific locus of the template. The forward and reverse primers of a primer pair may be designed to amplify a nucleic acid fragment of any suitable size to detect the presence of, for example, an allele of a SNV target according to the disclosure. Any one of the methods provided herein can include one or more steps for obtaining one or more primer pairs as described herein.

It should be appreciated that the primer pairs described herein may be used in a multiplex amplification-based quantification assay, such as a PCR assay. Accordingly, in some embodiments of any one of the methods or compositions provided herein, the primer pairs are designed to be compatible with other primer pairs in a PCR reaction. For example, the primer pairs may be designed to be compatible with at least 1, at least 2, at least 3, at least 4, at least 5, etc. other primer pairs in a PCR reaction. As used herein, primer pairs in a PCR reaction are "compatible" if they are capable of amplifying their target in the same PCR reaction. In some embodiments, primer pairs are compatible if the primer pairs are inhibited from amplifying their target DNA by no more than 1%, no more than 2%, no more than 3%, no more than 4%, no more than 5%, no more than 10%, no more than 15%, no more than 20%, no more than 25%, no more than 30%, no more than 35%, no more than 40%, no more than 45%, no more than 50%, or no more than 60% when multiplexed in the same PCR reaction. Primer pairs may not be compatible for a number of reasons including, but not limited to, the formation of primer dimers and binding to off-target sites on a template that may interfere with another primer pair. Accordingly, the primer pairs of the disclosure may be designed to prevent the formation of dimers with other primer pairs or limit the number of off-target binding sites. Exemplary methods for designing primers for use in a multiplex PCR assay are known in the art or otherwise described herein.

In some embodiments, the primer pairs described herein are used in a multiplex amplification-based quantification assay, such as a PCR assay, to quantify an amount of total nucleic acids. Accordingly, in some embodiments of any one of the methods or compositions provided herein, the primer pairs are designed to detect genomic regions that are diploid, excluding primer pairs that are designed to detect genomic regions that are potentially non-diploid. In some embodiments of any one of the methods or compositions provided herein, the primer pairs used in accordance with the disclosure do not detect repeat-masked regions, known copy-number variable regions, or other genomic regions that may be non-diploid.

In some embodiments of any one of the methods provided herein, the amplification-based quantitative assay is any quantitative assay, such as whereby nucleic acids are amplified and the amounts of the nucleic acids can be determined. Such assays include those whereby nucleic acids are amplified with the MOMA primers as described herein and quantified. Such assays include simple amplification and detection, hybridization techniques, separation technologies, such as electrophoresis, next generation sequencing and the like.

In some embodiments of any one of the methods provided herein the PCR is quantitative PCR meaning that amounts of nucleic acids can be determined. Quantitative PCR include real-time PCR, digital PCR, TAQMANTM, etc. In some embodiments of any one of the methods provided herein the PCR is "real-time PCR". Such PCR refers to a PCR reaction where the reaction kinetics can be monitored in the liquid phase while the amplification process is still proceeding. In contrast to conventional PCR, real-time PCR offers the ability to simultaneously detect or quantify in an amplification reaction in real time. Based on the increase of the fluorescence intensity from a specific dye, the concentration of the target can be determined even before the amplification reaches its plateau.

The use of multiple probes can expand the capability of single-probe real-time PCR. Multiplex real-time PCR uses multiple probe-based assays, in which each assay can have a specific probe labeled with a unique fluorescent dye, resulting in different observed colors for each assay. Real-time PCR instruments can discriminate between the fluorescence generated from different dyes. Different probes can be labeled with different dyes that each have unique emission spectra. Spectral signals are collected with discrete optics, passed through a series of filter sets, and collected by an array of detectors. Spectral overlap between dyes may be corrected by using pure dye spectra to deconvolute the experimental data by matrix algebra.

A probe may be useful for methods of the present disclosure, particularly for those methods that include a quantification step. Any one of the methods provided herein can include the use of a probe in the performance of the PCR assay(s), while any one of the compositions or kits provided herein can include one or more probes. Importantly, in some embodiments of any one or more of the methods provided herein, the probe in one or more or all of the PCR quantification assays is on the same strand as the mismatch primer and not on the opposite strand. It has been found that in so incorporating the probe in a PCR reaction, additional allele specific discrimination can be provided.

As an example, a TAQMAN™ probe is a hydrolysis probe that has a FAM™ or VIC® dye label on the 5' end, and minor groove binder (MGB) non-fluorescent quencher (NFQ) on the 3' end. The TAQMAN™ probe principle generally relies on the 5'-3' exonuclease activity of Taq® polymerase to cleave the dual-labeled TAQMAN™ probe during hybridization to a complementary probe-binding region and fluorophore-based detection. TAQMAN™ probes can increase the specificity of detection in quantitative measurements during the exponential stages of a quantitative PCR reaction.

PCR systems generally rely upon the detection and quantitation of fluorescent dyes or reporters, the signal of which increase in direct proportion to the amount of PCR product in a reaction. For example, in the simplest and most economical format, that reporter can be the double-stranded DNA-specific dye SYBR® Green (Molecular Probes). SYBR® Green is a dye that binds the minor groove of double-stranded DNA. When SYBR® Green dye binds to a double-stranded DNA, the fluorescence intensity increases. As more double-stranded amplicons are produced, SYBR® Green dye signal will increase.

It should be appreciated that the PCR conditions provided herein may be modified or optimized to work in accordance with any one of the methods described herein. Typically, the PCR conditions are based on the enzyme used, the target template, and/or the primers. In some embodiments, one or more components of the PCR reaction is modified or optimized. Non-limiting examples of the components of a PCR reaction that may be optimized include the template DNA, the primers (e.g., forward primers and reverse primers), the deoxynucleotides (dNTPs), the polymerase, the magnesium concentration, the buffer, the probe (e.g., when performing real-time PCR), the buffer, and the reaction volume.

In any of the foregoing embodiments, any DNA polymerase (enzyme that catalyzes polymerization of DNA nucleotides into a DNA strand) may be utilized, including thermostable polymerases. Suitable polymerase enzymes will be known to those skilled in the art, and include E. coli DNA polymerase, Klenow fragment of E. coli DNA polymerase I, T7 DNA polymerase, T4 DNA polymerase, T5 DNA polymerase, Klenow class polymerases, Taq polymerase, Pfu DNA polymerase, Vent polymerase, bacteriophage 29, REDTaq™ Genomic DNA polymerase, or sequenase. Exemplary polymerases include, but are not limited to Bacillus stearothermophilus pol I, Thermus aquaticus (Taq) pol I, Pyrccoccus furiosus (Pfu), Pyrccoccus woesei (Pwo), Thermus flavus (Tfl), Thermus thermophilus (Tth), Thermus litoris (Tli) and Thermotoga maritime (Tma). These enzymes, modified versions of these enzymes, and combination of enzymes, are commercially available from vendors including Roche, Invitrogen, Qiagen, Stratagene, and Applied Biosystems. Representative enzymes include PHUSION® (New England Biolabs, Ipswich, Mass.), Hot MasterTaq™ (Eppendorf), PHUSION® Mpx (Finnzymes), PyroStart® (Fermentas), KOD (EMD Biosciences), Z-Taq (TAKARA), and CS3AC/LA (KlenTaq, University City, Mo.

Salts and buffers include those familiar to those skilled in the art, including those comprising $MgCl_2$, and Tris-HCl and KCl, respectively. Typically, 1.5-2.0 nM of magnesium is optimal for Taq DNA polymerase, however, the optimal magnesium concentration may depend on template, buffer, DNA and dNTPs as each has the potential to chelate magnesium. If the concentration of magnesium $[Mg^{2+}]$ is too low, a PCR product may not form. If the concentration of magnesium $[Mg^{2+}]$ is too high, undesired PCR products may be seen. In some embodiments the magnesium concentration may be optimized by supplementing magnesium concentration in 0.1 mM or 0.5 mM increments up to about 5 mM.

Buffers used in accordance with the disclosure may contain additives such as surfactants, dimethyl sulfoxide (DMSO), glycerol, bovine serum albumin (BSA) and polyethylene glycol (PEG), as well as others familiar to those skilled in the art. Nucleotides are generally deoxyribonucleoside triphosphates, such as deoxyadenosine triphosphate (dATP), deoxycytidine triphosphate (dCTP), deoxyguanosine triphosphate (dGTP), and deoxythymidine triphosphate (dTTP), which are also added to a reaction adequate amount for amplification of the target nucleic acid. In some embodiments, the concentration of one or more dNTPs (e.g., dATP, dCTP, dGTP, dTTP) is from about 10 µM to about 500 µM which may depend on the length and number of PCR products produced in a PCR reaction.

In some embodiments, the concentration of primers used in the PCR reaction may be modified or optimized. In some embodiments, the concentration of a primer (e.g., a forward or reverse primer) in a PCR reaction may be, for example, about 0.05 µM to about 1 µM. In particular embodiments, the concentration of each primer is about 1 nM to about 1 µM. It should be appreciated that the primers in accordance with the disclosure may be used at the same or different concentrations in a PCR reaction. For example, the forward primer of a primer pair may be used at a concentration of 0.5 µM and the reverse primer of the primer pair may be used at 0.1 µM. The concentration of the primer may be based on factors including, but not limited to, primer length, GC content, purity, mismatches with the target DNA or likelihood of forming primer dimers.

In some embodiments, the thermal profile of the PCR reaction is modified or optimized. Non-limiting examples of PCR thermal profile modifications include denaturation temperature and duration, annealing temperature and duration and extension time.

The temperature of the PCR reaction solutions may be sequentially cycled between a denaturing state, an annealing state, and an extension state for a predetermined number of cycles. The actual times and temperatures can be enzyme, primer, and target dependent. For any given reaction, denaturing states can range in certain embodiments from about 70° C. to about 100° C. In addition, the annealing temperature and time can influence the specificity and efficiency of primer binding to a particular locus within a target nucleic acid and may be important for particular PCR reactions. For any given reaction, annealing states can range in certain embodiments from about 20° C. to about 75° C. In some embodiments, the annealing state can be from about 46° C. to 64° C. In certain embodiments, the annealing state can be performed at room temperature (e.g., from about 20° C. to about 25° C.).

Extension temperature and time may also impact the allele product yield. For a given enzyme, extension states can range in certain embodiments from about 60° C. to about 75° C.

Quantification of the amounts of the alleles from a PCR assay can be performed as provided herein or as otherwise would be apparent to one of ordinary skill in the art. As an example, amplification traces are analyzed for consistency and robust quantification. Internal standards may be used to translate the cycle threshold to amount of input nucleic acids (e.g., DNA). The amounts of alleles can be computed as the mean of performant assays and can be adjusted for genotype.

Other methods for determining total cell-free DNA in a sample are known in the art.

In some embodiments of any one of the methods provided herein, the total cell-free DNA is determined with TAQMAN™ Real-time PCR using RNase P as a target.

Any one of the methods provided herein can comprise extracting nucleic acids, such as total-free DNA, from a sample obtained from a subject. Such extraction can be done using any method known in the art or as otherwise provided herein (see, e.g., Current Protocols in Molecular Biology, latest edition, or the QlAamp circulating nucleic acid kit or other appropriate commercially available kits). An exemplary method for isolating cell-free DNA from blood is described. Blood containing an anti-coagulant such as EDTA or DTA is collected from a subject. The plasma, which contains cf-DNA, is separated from cells present in the blood (e.g., by centrifugation or filtering). An optional secondary separation may be performed to remove any remaining cells from the plasma (e.g., a second centrifugation or filtering step). The cf-DNA can then be extracted using any method known in the art, e.g., using a commercial kit such as those produced by Qiagen. Other exemplary methods for extracting cf-DNA are also known in the art (see, e.g., Cell-Free Plasma DNA as a Predictor of Outcome in Severe Sepsis and Septic Shock. Clin. Chem. 2008, v. 54, p. 1000-1007; Prediction of MYCN Amplification in Neuroblastoma Using Serum DNA and Real-Time Quantitative Polymerase Chain Reaction. JCO 2005, v. 23, p.5205-5210; Circulating Nucleic Acids in Blood of Healthy Male and Female Donors. Clin. Chem. 2005, v. 51, p.1317-1319; Use of Magnetic Beads for Plasma Cell-free DNA Extraction: Toward Automation of Plasma DNA Analysis for Molecular Diagnostics. Clin. Chem. 2003, v. 49, p. 1953-1955; Chiu R W K, Poon L L M, Lau T K, Leung T N, Wong E M C, Lo Y M D. Effects of blood-processing protocols on fetal and total DNA quantification in maternal plasma. Clin Chem 2001; 47:1607-1613; and Swinkels et al. Effects of Blood-Processing Protocols on Cell-free DNA Quantification in Plasma. Clinical Chemistry, 2003, vol. 49, no. 3, 525-526).

In some embodiments of any one of the methods provided herein, a pre-amplification step is performed. An exemplary method of such an amplification is as follows, and such a method can be included in any one of the methods provided herein. Approximately 15 ng of cell-free plasma DNA is amplified in a PCR using Q5 DNA polymerase with approximately 13 targets where pooled primers were at 4 uM total. Samples undergo approximately 25 cycles. Reactions are in 25 ul total. After amplification, samples can be cleaned up using several approaches including AMPURE bead cleanup, bead purification, or simply ExoSAP-IT™, or Zymo.

As used herein, the sample from a subject can be a biological sample. Examples of such biological samples include whole blood, plasma, serum, urine, etc. In some embodiments, addition of further nucleic acids, e.g., a standard, to the sample can be performed.

In another aspect, compositions and kits comprising one or more primer pairs as provided herein are provided. Other reagents for performing an assay, such as a PCR assay, may also be included in the composition or kit.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different from illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The following description provides examples of the methods provided herein.

EXAMPLES

Example 1

Examples of Computer-Implemented Embodiments

Figure 2:
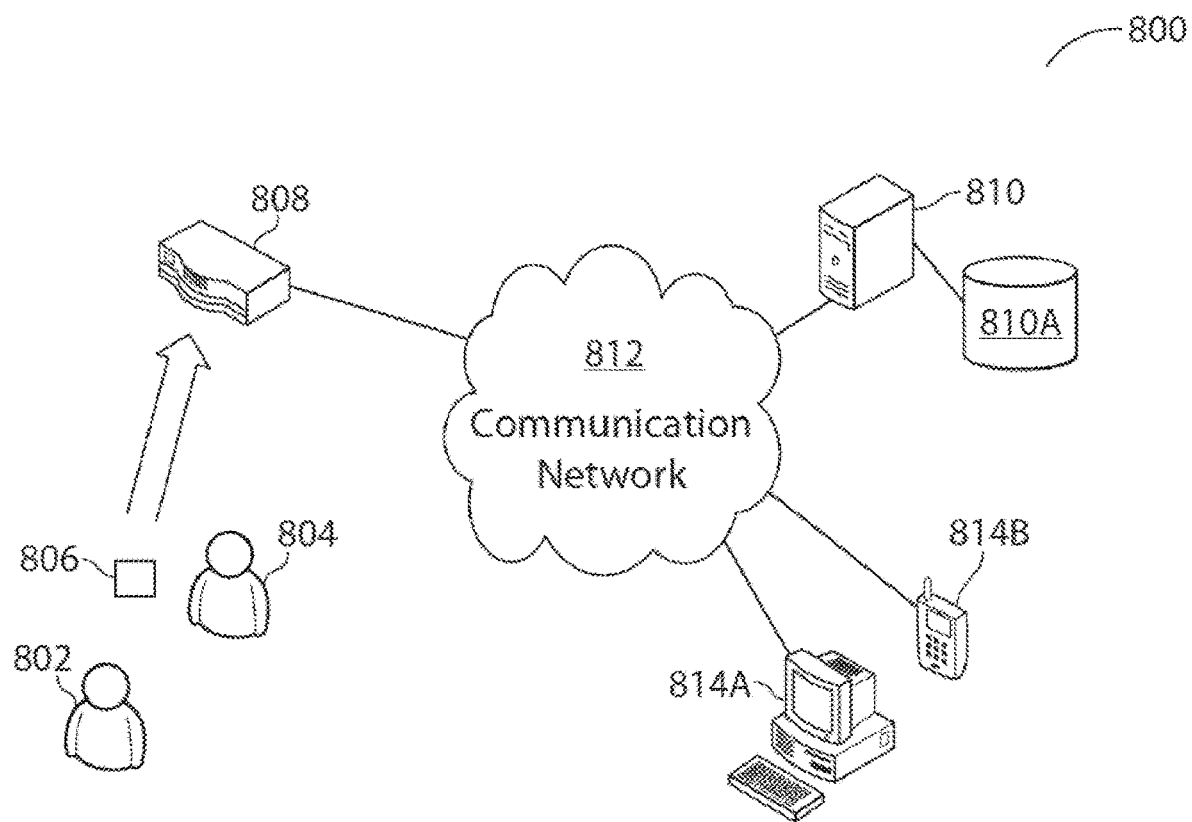
FIG. 2 illustrates an example of a computer system with which some embodiments may operate.
Figure 3:
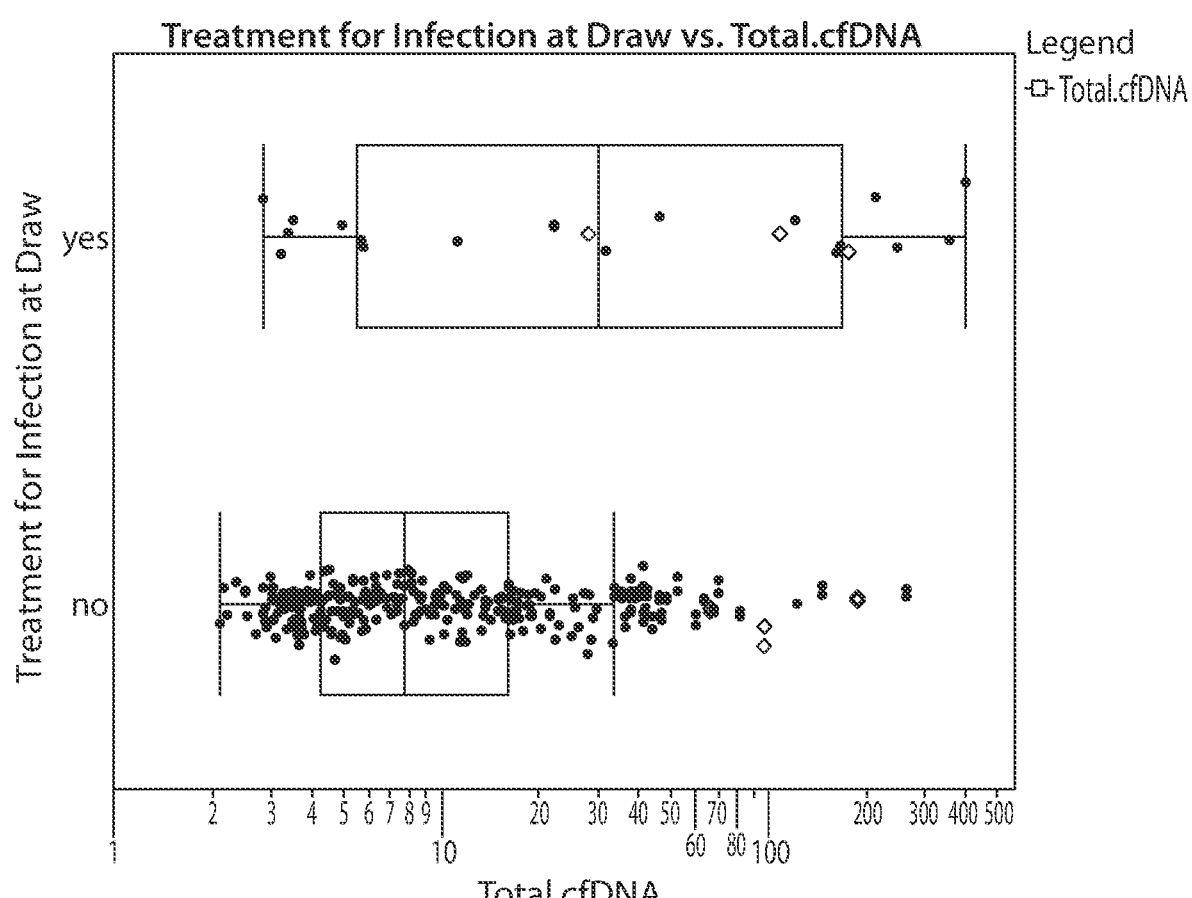
FIG. 3 is a graph depicting the total cell-free DNA (cf-DNA) of different samples and whether or not the subject was undergoing treatment for infection at the time of the sample.
Figure 4:
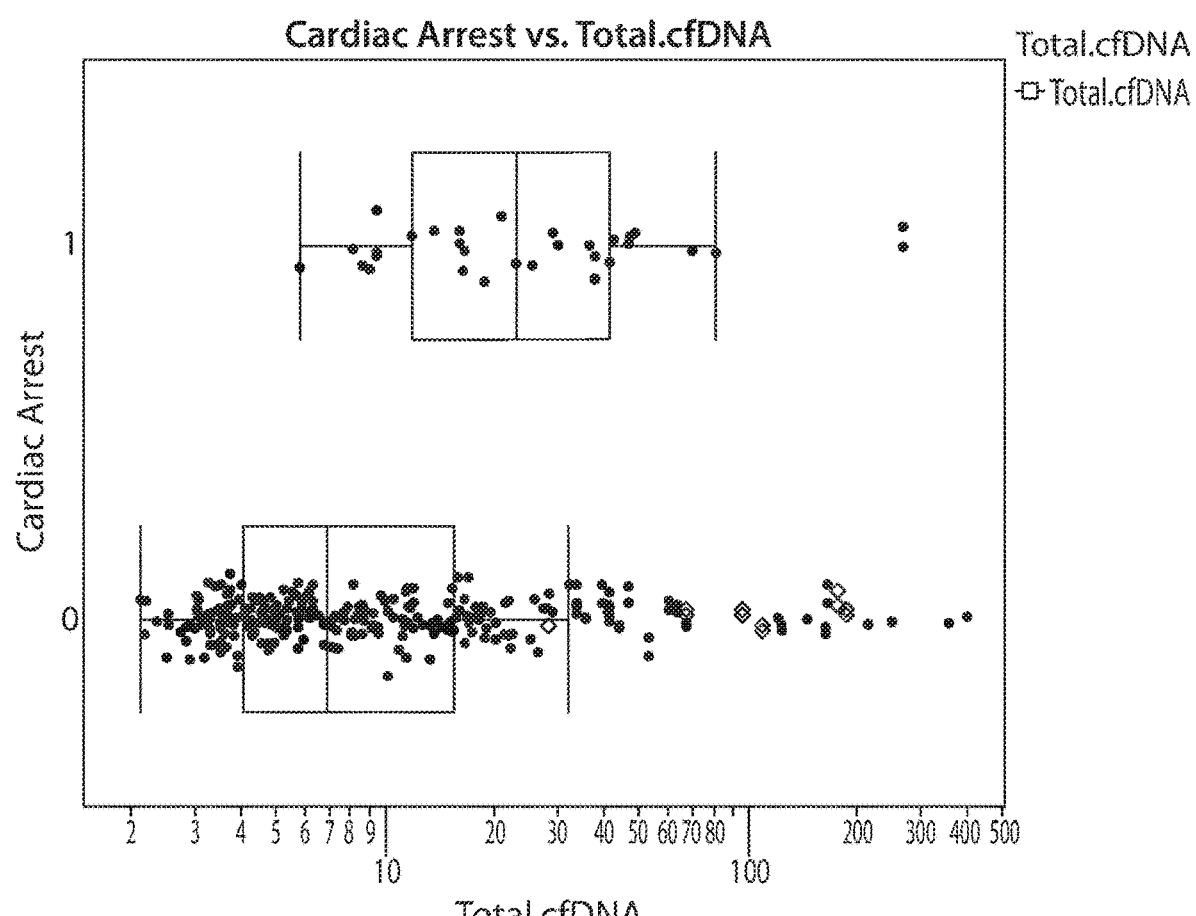
FIG. 4 is a graph depicting the total cell-free DNA (cf-DNA) of different samples and whether each subject went into cardiac arrest (1) or did not (0).
Figure 5:
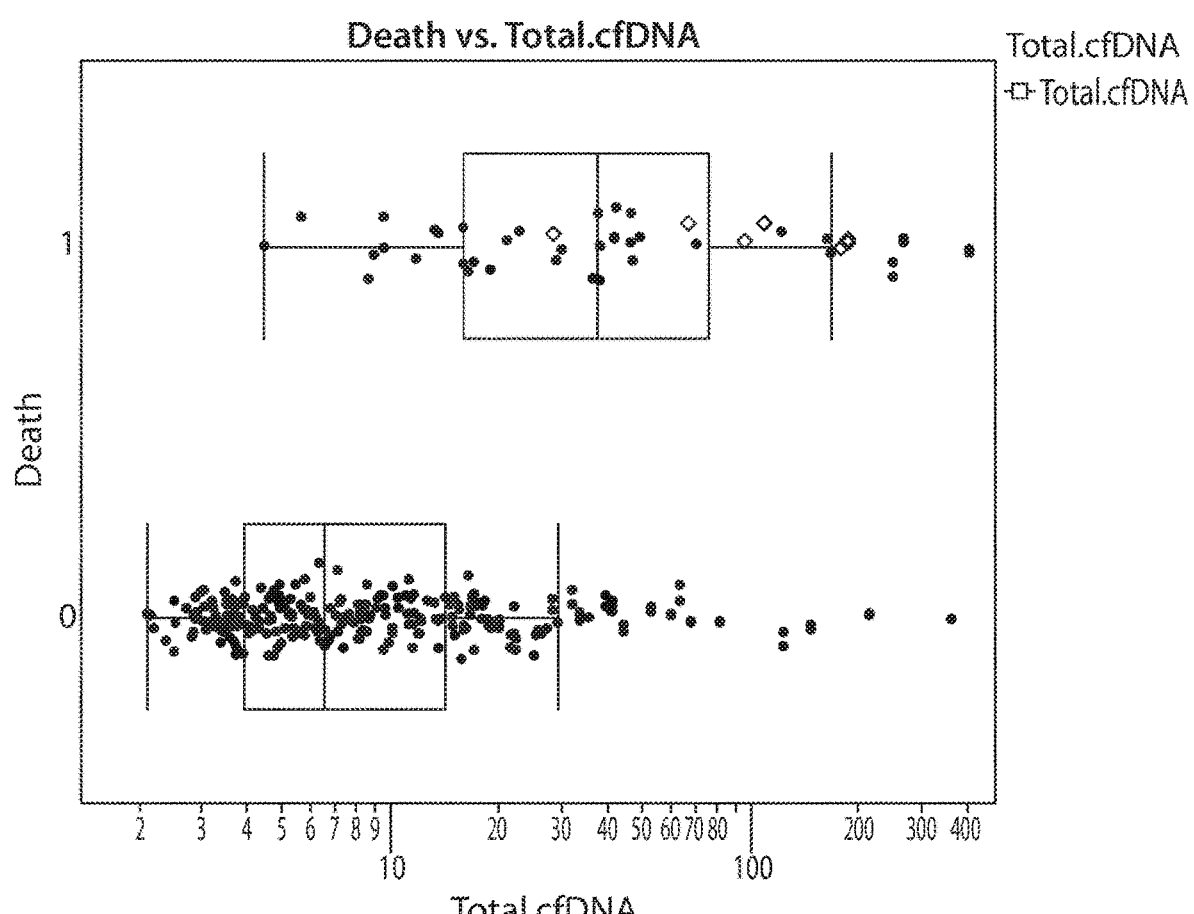
FIG. 5 is a graph depicting the total cell-free DNA (cf-DNA) of different samples and whether each subject died (1) or survived (0).
Figure 6:
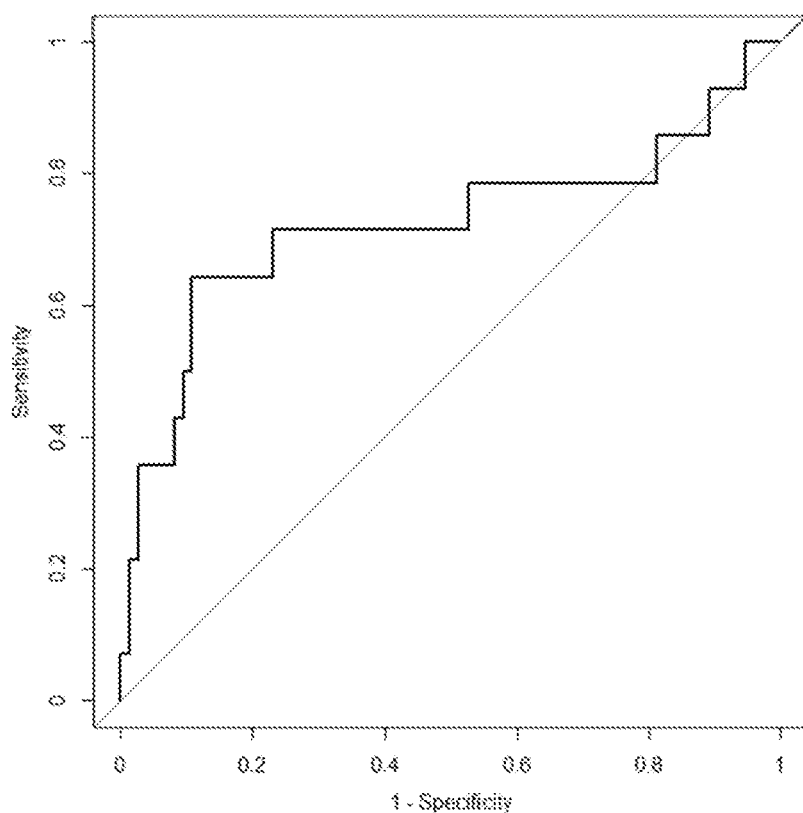
FIG. 6 is a graph showing the experimental determination of a cutpoint (threshold) for infection using the final sample from each subject (N=88).
Figure 7:
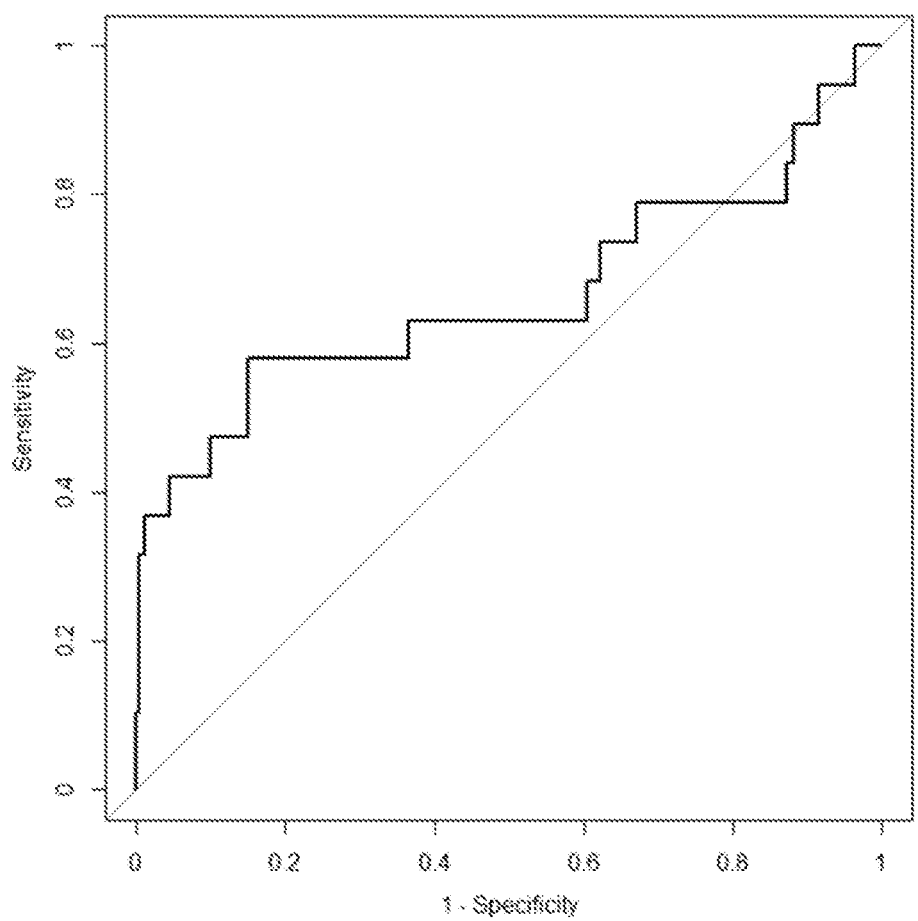
FIG. 7 is a graph showing the experimental determination of a cutpoint (threshold) for infection using total cf-DNA and excluding those subjects on mechanical support (N=292).
Figure 8:
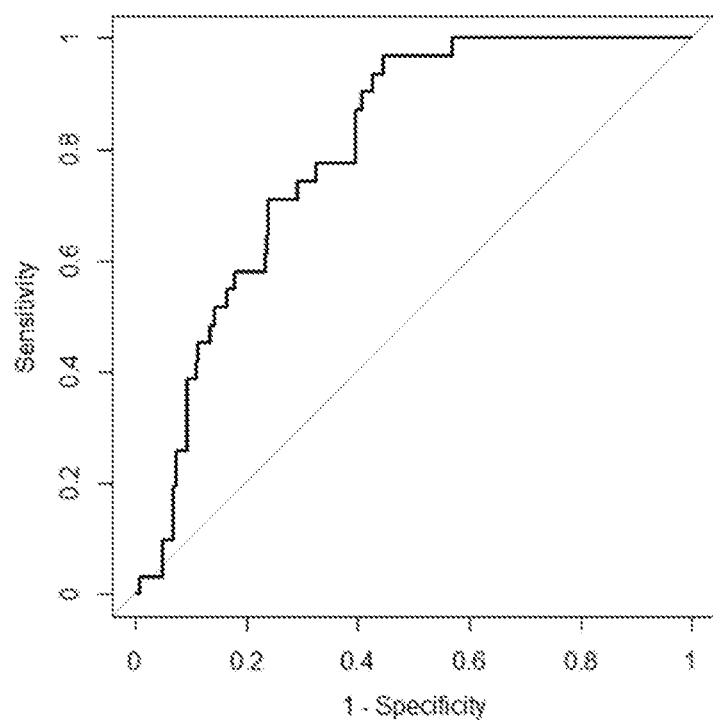
FIG. 8 is a graph showing the experimental determination of a cutpoint (threshold) for cardiac arrest using total cf-DNA from 298 samples.
Figure 9:
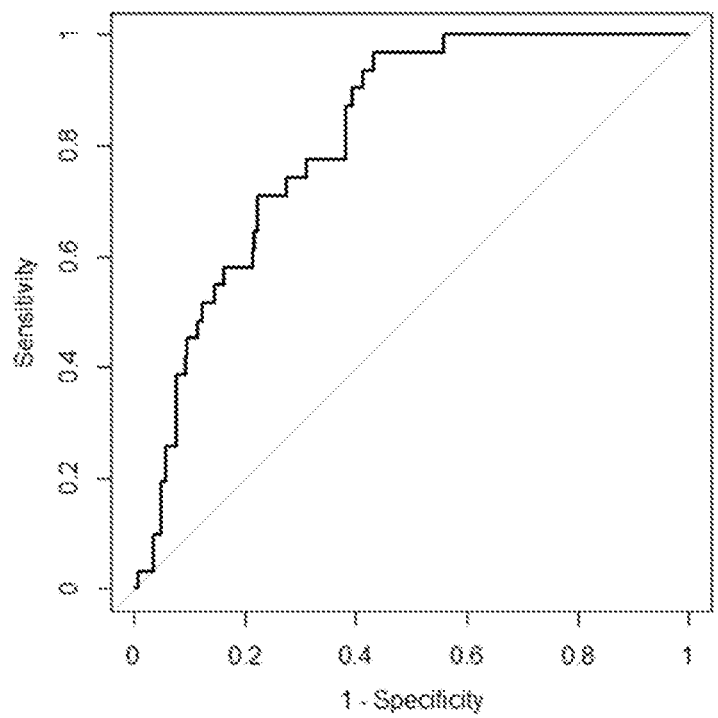
FIG. 9 is a graph showing the experimental determination of a cutpoint (threshold) for cardiac arrest using total cf-DNA from 292 samples. Samples from subjects on mechanical support were excluded from the analysis.
Figure 10:
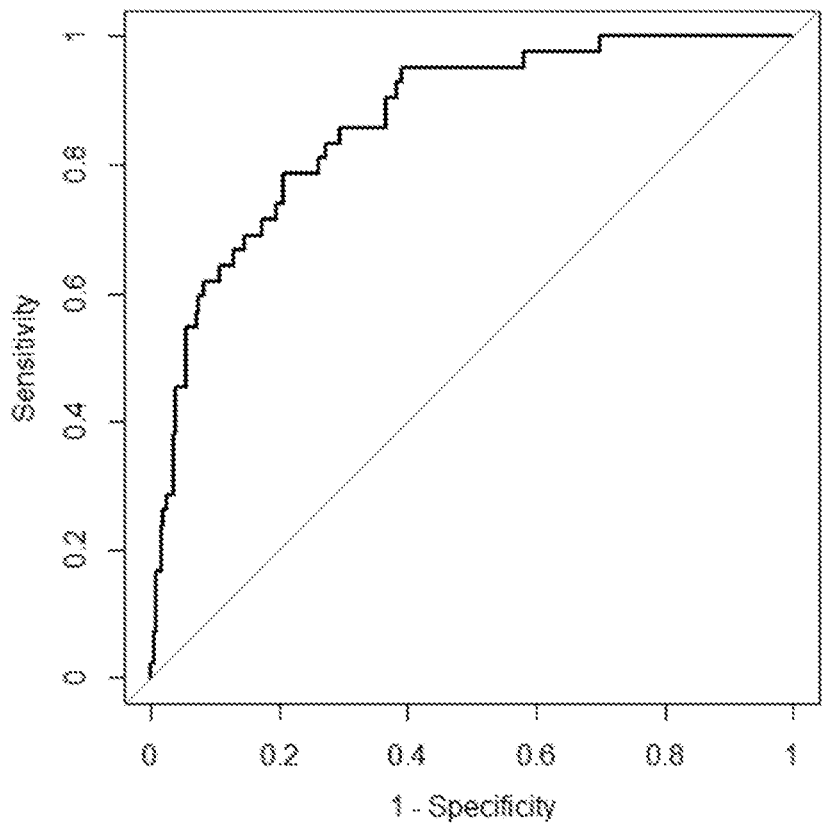
FIG. 10 is a graph showing the experimental determination of a cutpoint (threshold) for death using total cf-DNA from 298 samples.
Figure 11:
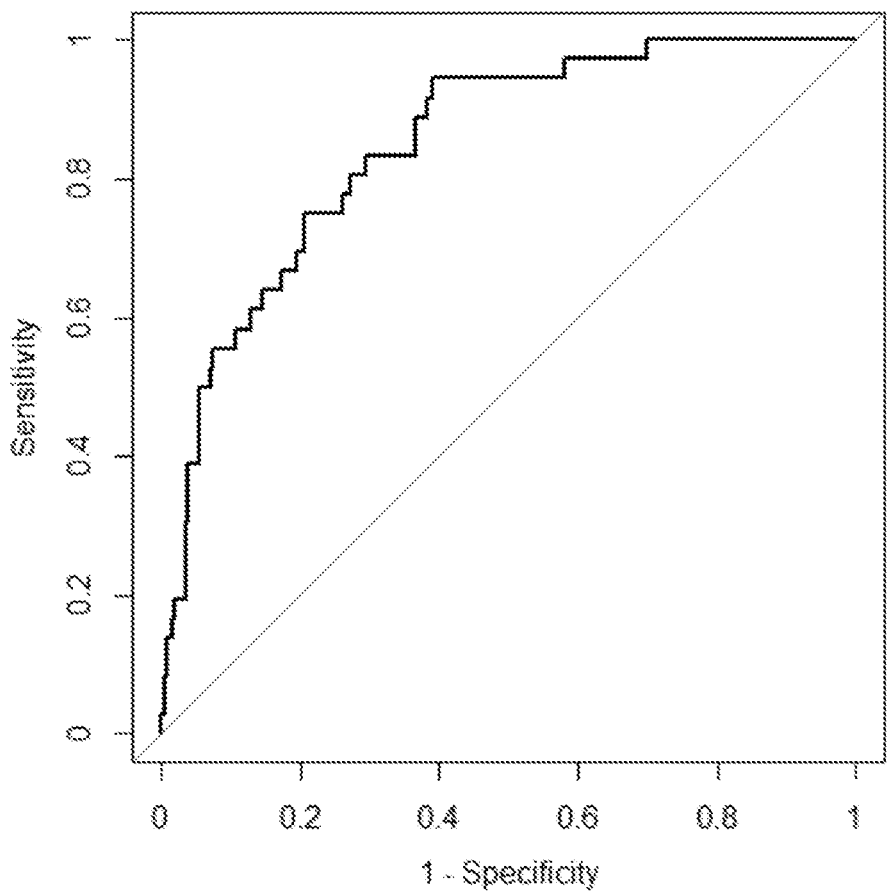
FIG. 11 is a graph showing the experimental determination of a cutpoint (threshold) for death using total cf-DNA. Samples from subjects on mechanical support were excluded from the analysis.
Figure 12:
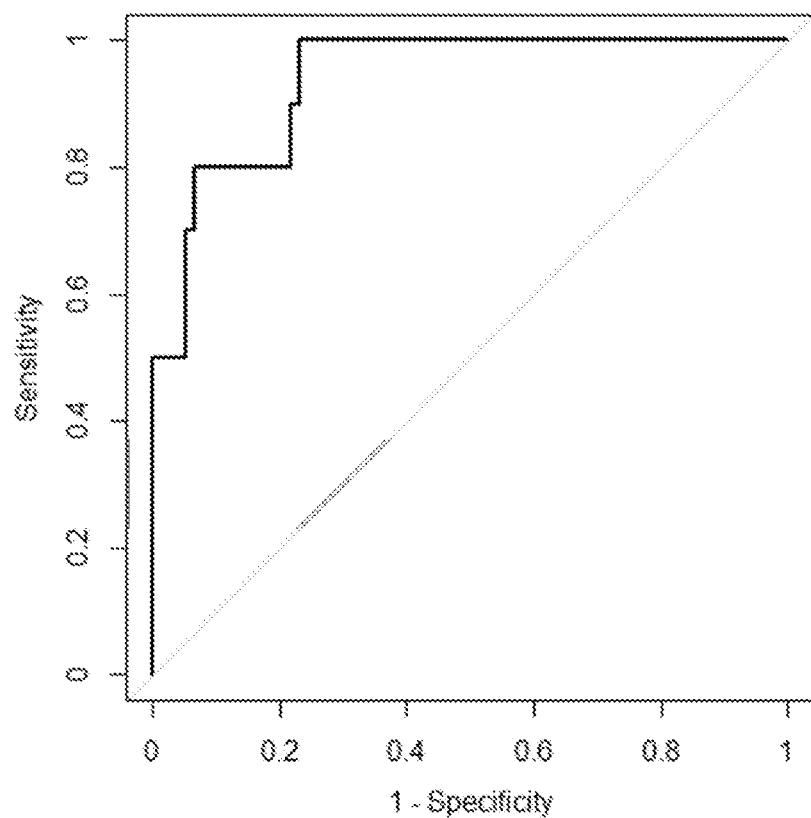
FIG. 12 is a graph showing the experimental determination of a cutpoint (threshold) for death using total cf-DNA from the final sample from each subject (N=88).
Figure 13:
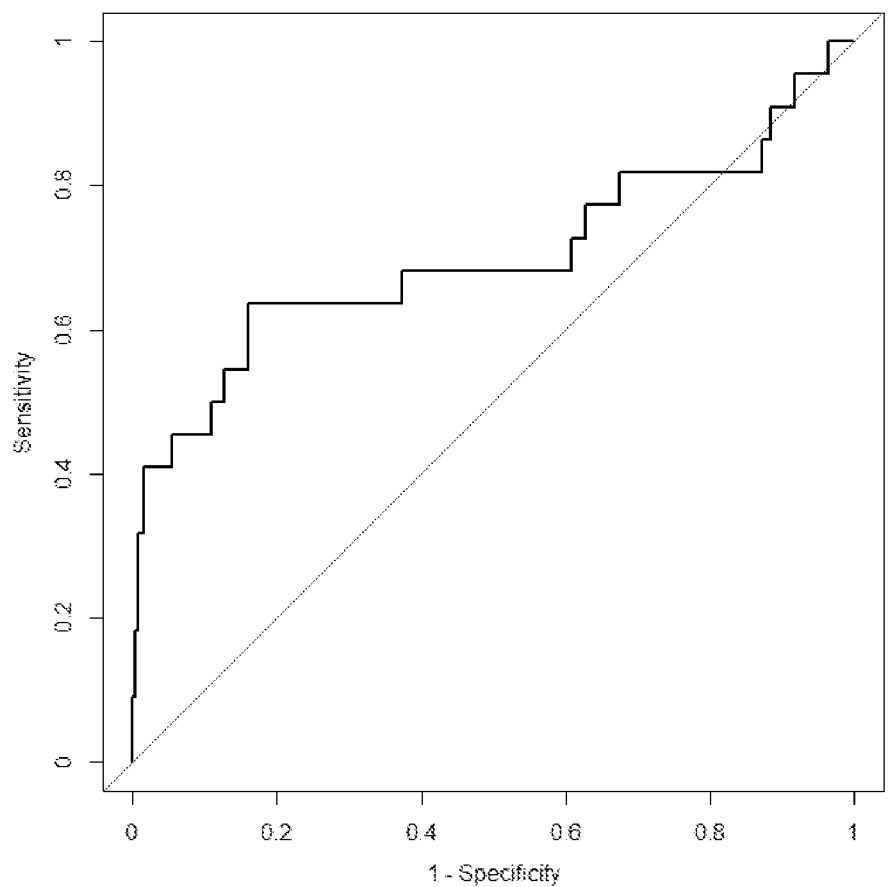
FIG. 13 is a graph showing the experimental determination of a cutpoint (threshold) for infection using total cf-DNA from 298 samples.
Figure 14:
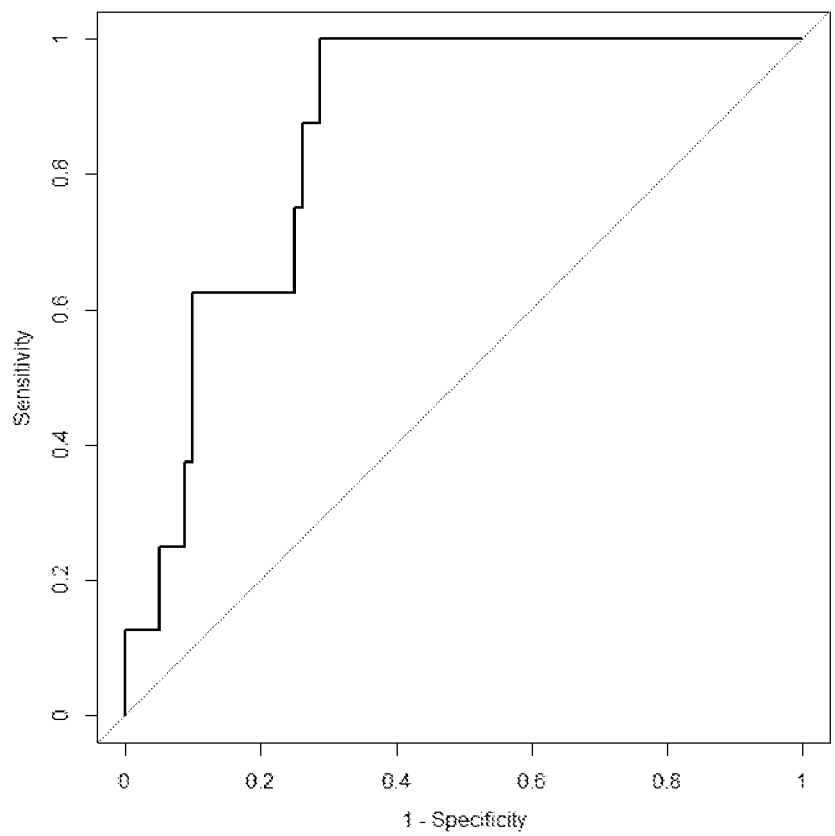
FIG. 14 is a graph showing the experimental determination of a cutpoint (threshold) for cardiac arrest using total cf-DNA from the final sample of each subject (N=88).
Figure 16:
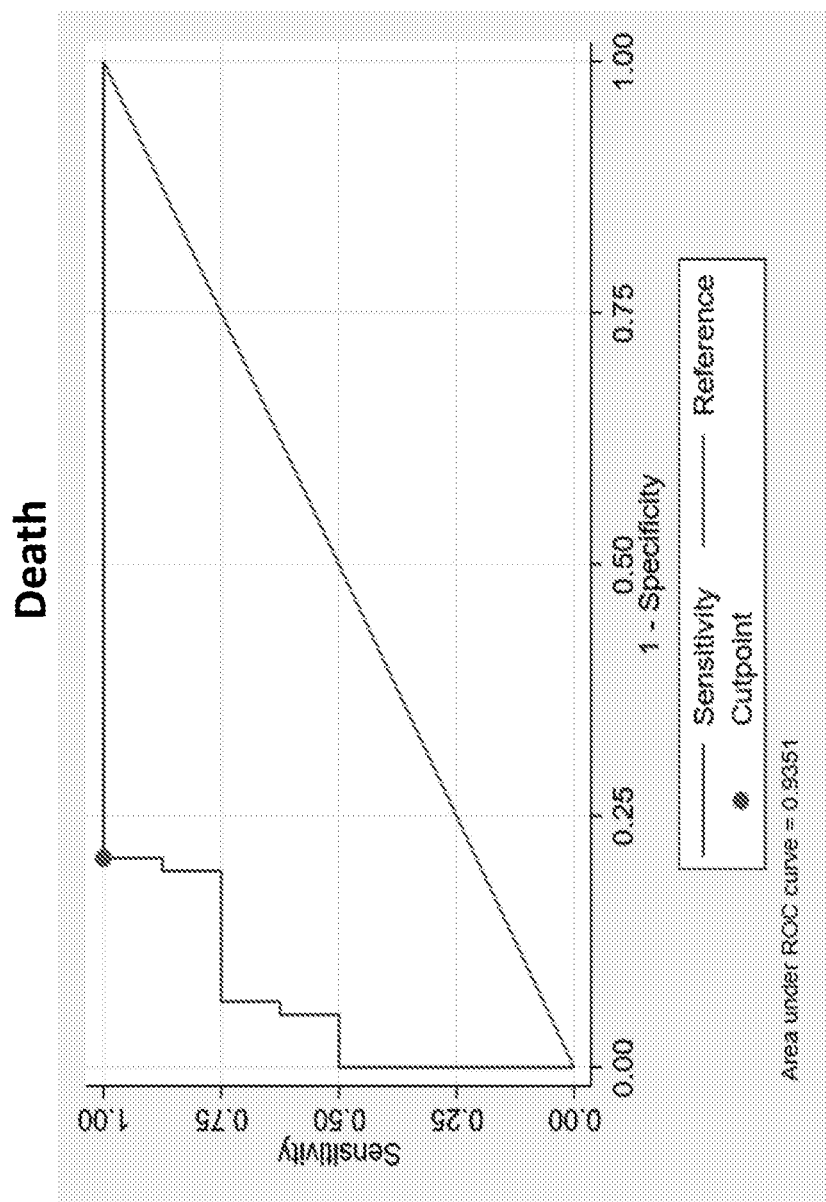
FIG. 16 is a graphical representation of the results of FIG. 15, showing the experimental determination of a cutpoint (threshold) for death using total cf-DNA from the 85 samples.
Figure 18:
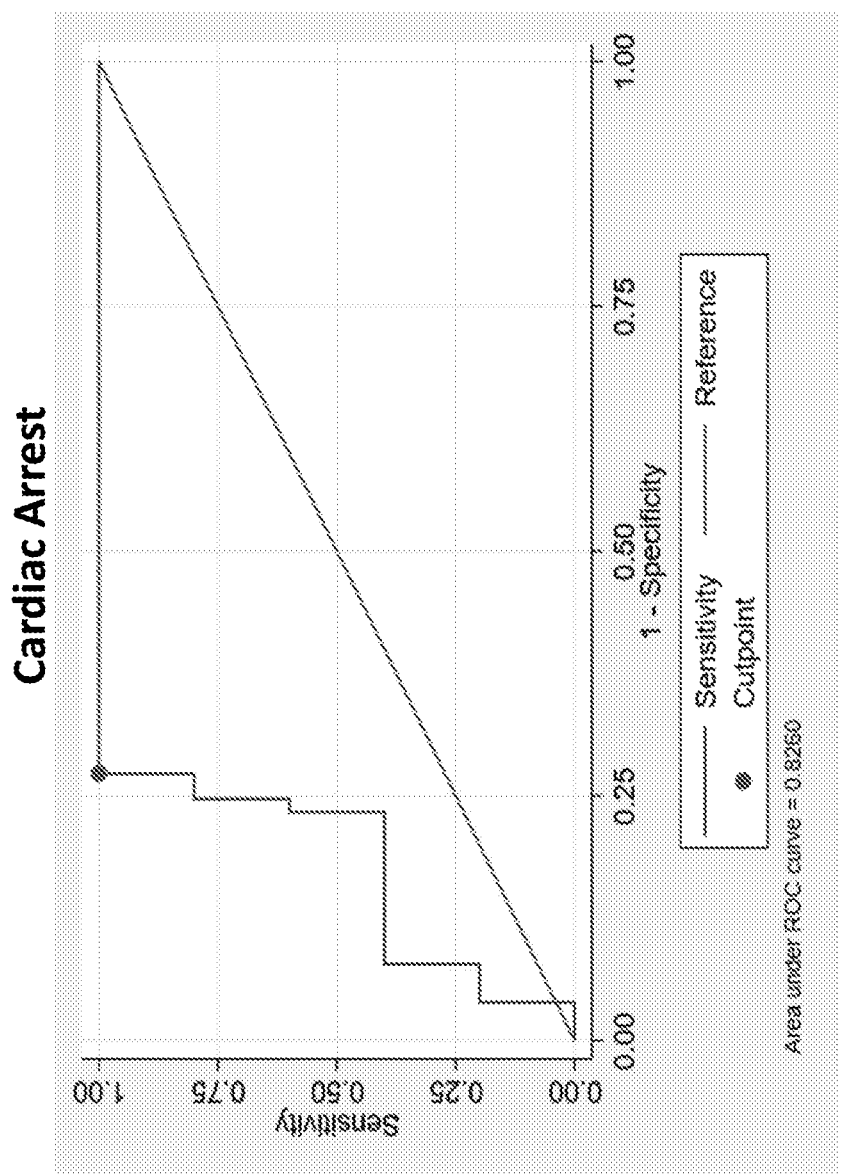
FIG. 18 is a graphical representation of the results of FIG. 17, showing the experimental determination of a cutpoint (threshold) for cardiac arrest using total cf-DNA from the 85 samples.
Figure 20:
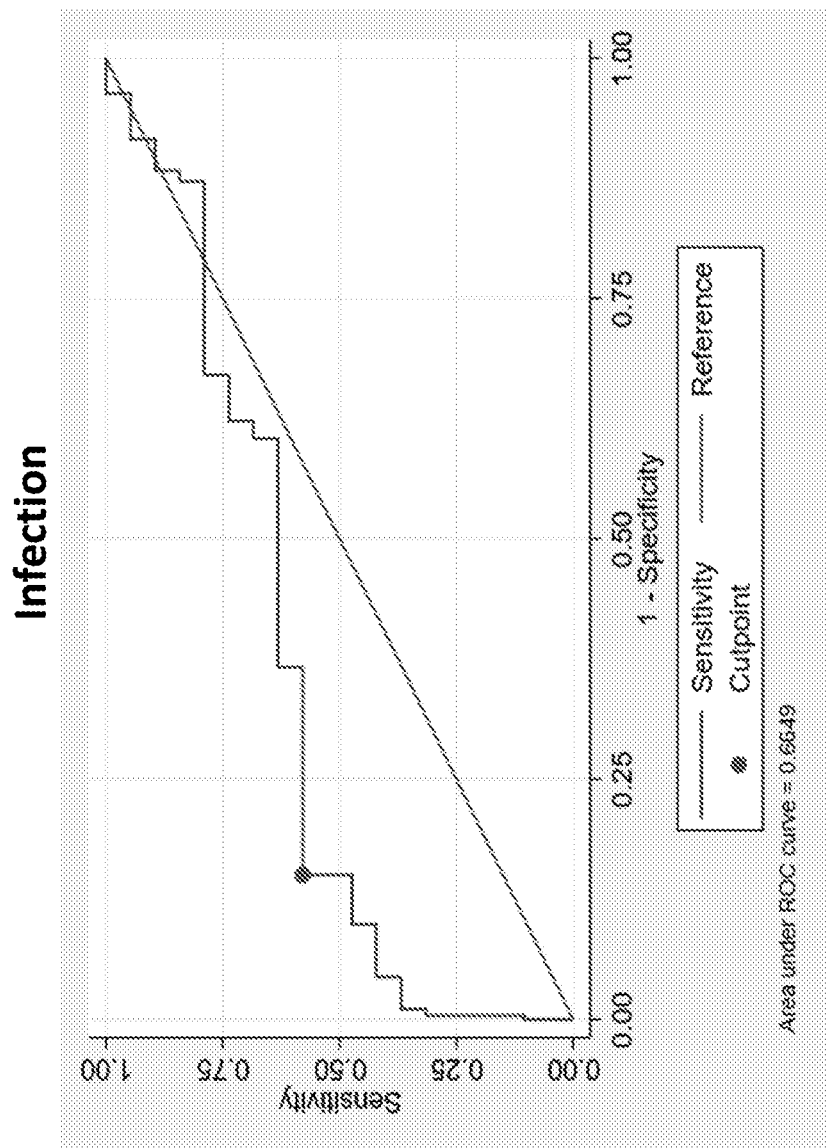
FIG. 20 is a graphical representation of the results of FIG. 19, showing the experimental determination of a cutpoint (threshold) for infection (i.e., whether the subject was undergoing treatment for infection at the time of the sample) using total cf-DNA from the 292 samples.

In some embodiments, the diagnostic techniques described above may be implemented via one or more computing devices executing one or more software facilities to analyze samples for a subject over time, measure nucleic acids (such as cell-free DNA) in the samples, and produce a diagnostic result based on one or more of the samples. FIG. 2 illustrates an example of a computer system with which some embodiments may operate, though it should be appreciated that embodiments are not limited to operating with a system of the type illustrated in FIG. 2.

The computer system of FIG. 2 includes a subject 802 and a clinician 804 that may obtain a sample 806 from the subject 806. As should be appreciated from the foregoing, the sample 806 may be any suitable sample of biological material for the subject 802 that may be used to measure the presence of nucleic acids (such as cell-free DNA) in the subject 802, including a blood sample. The sample 806 may be provided to an analysis device 808, which one of ordinary skill will appreciate from the foregoing will analyze the sample 808 so as to determine (including estimate) a total amount of nucleic acids (such as cell-free DNA) in the sample 806 and/or the subject 802. For ease of illustration, the analysis device 808 is depicted as single device, but it should be appreciated that analysis device 808 may take any suitable form and may, in some embodiments, be implemented as multiple devices. To determine the amounts of nucleic acids (such as cell-free DNA) in the sample 806 and/or subject 802, the analysis device 808 may perform any of the techniques described above, and is not limited to performing any particular analysis. The analysis device 808 may include one or more processors to execute an analysis facility implemented in software, which may drive the processor(s) to operate other hardware and receive the results of tasks performed by the other hardware to determine on overall result of the analysis, which may be the amounts of nucleic acids (such as cell-free DNA) in the sample 806 and/or the subject 802. The analysis facility may be stored in one or more computer-readable storage media, such as a memory of the device 808. In other embodiments, techniques described herein for analyzing a sample may be partially or entirely implemented in one or more special-purpose computer components such as Application Specific Integrated Circuits (ASICs), or through any other suitable form of computer component that may take the place of a software implementation.

In some embodiments, the clinician 804 may directly provide the sample 806 to the analysis device 808 and may operate the device 808 in addition to obtaining the sample 806 from the subject 802, while in other embodiments the device 808 may be located geographically remote from the clinician 804 and subject 802 and the sample 806 may need to be shipped or otherwise transferred to a location of the analysis device 808. The sample 806 may in some embodiments be provided to the analysis device 808 together with (e.g., input via any suitable interface) an identifier for the sample 806 and/or the subject 802, for a date and/or time at which the sample 806 was obtained, or other information describing or identifying the sample 806.

The analysis device 808 may in some embodiments be configured to provide a result of the analysis performed on the sample 806 to a computing device 810, which may include a data store 810A that may be implemented as a database or other suitable data store. The computing device 810 may in some embodiments be implemented as one or more servers, including as one or more physical and/or virtual machines of a distributed computing platform such as a cloud service provider. In other embodiments, the device 810 may be implemented as a desktop or laptop personal computer, a smart mobile phone, a tablet computer, a special-purpose hardware device, or other computing device.

In some embodiments, the analysis device 808 may communicate the result of its analysis to the device 810 via one or more wired and/or wireless, local and/or wide-area computer communication networks, including the Internet. The result of the analysis may be communicated using any suitable protocol and may be communicated together with the information describing or identifying the sample 806, such as an identifier for the sample 806 and/or subject 802 or a date and/or time the sample 806 was obtained.

The computing device 810 may include one or more processors to execute a diagnostic facility implemented in software, which may drive the processor(s) to perform diagnostic techniques described herein. The diagnostic facility may be stored in one or more computer-readable storage media, such as a memory of the device 810. In other embodiments, techniques described herein for analyzing a sample may be partially or entirely implemented in one or more special-purpose computer components such as Application Specific Integrated Circuits (ASICs), or through any other suitable form of computer component that may take the place of a software implementation.

The diagnostic facility may receive the result of the analysis and the information describing or identifying the sample 806 and may store that information in the data store 810A. The information may be stored in the data store 810A in association with other information for the subject 802, such as in a case that information regarding prior samples for the subject 802 was previously received and stored by the diagnostic facility. The information regarding multiple samples may be associated using a common identifier, such as an identifier for the subject 802. In some cases, the data store 810A may include information for multiple different subjects.

The diagnostic facility may also be operated to analyze results of the analysis of one or more samples 806 for a particular subject 802, identified by user input, so as to determine a diagnosis for the subject 802. The diagnosis may be a conclusion of a risk that the subject 802 has, may have, or may in the future develop a particular condition. The diagnostic facility may determine the diagnosis using any of the various examples described above, including by comparing the amounts of nucleic acids (such as cell-free DNA) determined for a particular sample 806 to one or more thresholds or by comparing a change over time in the amounts of nucleic acids (such as cell-free DNA) determined for samples 806 over time to one or more thresholds. For example, the diagnostic facility may determine a risk to the subject 802 of a condition by comparing a total amount of nucleic acids (such as cell-free DNA) for one or more samples 806 to a threshold. Based on the comparisons to the thresholds, the diagnostic facility may produce an output indicative of a risk to the subject 802 of a condition.

As should be appreciated from the foregoing, in some embodiments, the diagnostic facility may be configured with different thresholds to which amounts of nucleic acids (such as cell-free DNA) may be compared. The different thresholds may, for example, correspond to different demographic groups (age, gender, race, economic class, presence or absence of a particular procedure/condition/other in medical history, or other demographic categories), different conditions, and/or other parameters or combinations of parameters. In such embodiments, the diagnostic facility may be configured to select thresholds against which amounts of nucleic acids (such as cell-free DNA) are to be compared, with different thresholds stored in memory of the computing device 810. The selection may thus be based on demographic information for the subject 802 in embodiments in which thresholds differ based on demographic group, and in these cases demographic information for the subject 802 may be provided to the diagnostic facility or retrieved (from another computing device, or a data store that may be the same or different from the data store 810A, or from any other suitable source) by the diagnostic facility using an identifier for the subject 802. The selection may additionally or alternatively be based on the condition for which a risk is to be determined, and the diagnostic facility may prior to determining the risk receive as input a condition and use the condition to select the thresholds on which to base the determination of risk. It should be appreciated that the diagnostic facility is not limited to selecting thresholds in any particular manner, in embodiments in which multiple thresholds are supported.

In some embodiments, the diagnostic facility may be configured to output for presentation to a user a user interface that includes a diagnosis of a risk and/or a basis for the diagnosis for a subject 802. The basis for the diagnosis may include, for example, amounts of nucleic acids (such as cell-free DNA) detected in one or more samples 806 for a subject 802. In some embodiments, user interfaces may include any of the examples of results, values, amounts, graphs, etc. discussed above. They can include results, values, amounts, etc. over time. For example, in some embodiments, a user interface may incorporate a graph similar to that shown in any one of the figures provided herein. In such a case, in some cases the graph may be annotated to indicate to a user how different regions of the graph may correspond to different diagnoses that may be produced from an analysis of data displayed in the graph. For example, thresholds against which the graphed data may be compared to determine the analysis may be imposed on the graph(s).

A user interface including a graph, particularly with the lines and/or shading, may provide a user with a far more intuitive and faster-to-review interface to determine a risk of the subject 802 based on amounts of nucleic acids (such as cell-free DNA), than may be provided through other user interfaces. It should be appreciated, however, that embodiments are not limited to being implemented with any particular user interface.

In some embodiments, the diagnostic facility may output the diagnosis or a user interface to one or more other computing devices 814 (including devices 814A, 814B) that may be operated by the subject 802 and/or a clinician, which may be the clinician 804 or another clinician. The diagnostic facility may transmit the diagnosis and/or user interface to the device 814 via the network(s) 812.

Techniques operating according to the principles described herein may be implemented in any suitable manner. Included in the discussion above are a series of flow charts showing the steps and acts of various processes that determine a risk of a condition based on an analysis of amounts of nucleic acids (such as cell-free DNA). The processing and decision blocks discussed above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that embodiments are not limited to any particular syntax or operation of any particular circuit or of any particular programming language or type of programming language. Rather, one skilled in the art may use the description above to fabricate circuits or to implement computer software algorithms to perform the processing of a particular apparatus carrying out the types of techniques described herein. It should also be appreciated that, unless otherwise indicated herein, the particular sequence of steps and/or acts described above is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as a portion of a computing device or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

In some, but not all, implementations in which the techniques may be embodied as computer-executable instructions, these instructions may be executed on one or more suitable computing device(s) operating in any suitable computer system, including the exemplary computer system of FIG. 2, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, etc.). Functional facilities comprising these computer-executable instructions may be integrated with and direct the operation of a single multi-purpose programmable digital computing device, a coordinated system of two or more multi-purpose computing device sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments. Any one of the aforementioned, including the aforementioned devices, systems, embodiments, methods, techniques, algorithms, media, hardware, software, interfaces, processors, displays, networks, inputs, outputs or any combination thereof are provided herein in other aspects.

Example 2

Total Cell-free DNA (cf-DNA) Correlation with Transplant Complications

The total cf-DNA of transplant recipients was quantified using the methods described above. The correlation between total cf-DNA and different transplant complications was examined and the graphical results are presented in FIGS. 3-14.

Statistics of the death outcome analysis are presented in Table 1 below.

TABLE 1

Summary of Death Outcome Statistics

| | AUC | sensitivity | specificity | Cutoff | Repeated model |
|---|---|---|---|---|---|
| 1. Total cfDNA all 298 | 0.8664 | 0.786 | 0.793 | 15.96 | −1.9463 + 0.0023 * Total cfDNA (p = 0.03) |
| 2. Total cfDNA all 292 (Mech support excluded) | 0.8484 | 0.944 | 0.609 | 8.72 | −2.0805 + 0.0019 * Total cfDNA (p = 0.04) |
| 3. Last sample from all (n = 88) | 0.9385 | ~1.0 | 0.769 | 8.77 | −3.3358 + 0.0480 * Total cfDNA (p = 0.01) |

Example 3

Total Cell-free DNA (cf-DNA) Correlation with Transplant Complications

Blood samples were collected prospectively from heart transplant recipients around time of transplantation, any treatment for rejection, readmission, and prior to biopsy and/or angiography. Cf-DNA was quantified. The correlation between total cf-DNA and different transplant complications was examined and the tabular and graphical results are presented in FIGS. 15-20. Biopsy and angiography results, as well as cardiac arrest, death, and treatment for infection were correlated to cf-DNA levels at a cutpoint of 15 nanograms per milliliter (ng/mL). 298 samples from 88 recipients were analyzed. Cf-DNA of >15 ng/mL was strongly associated with death [p<0.001, OR 20.10 (95% CI 3.55-113.69)], and treatment for infection [p0.006, OR 3.50 (95% CI 1.36-9.03)]. Total circulating cf-DNA was strongly associated with death and treatment for infection at time of draw.

What is claimed is:

1. A method for preparing a preparation of amplified DNA from a sample from a transplant subject who is a heart transplant recipient for determining whether an amount of total cf-DNA is equal to or exceeds a threshold, the method comprising:
   (a) extracting cell-free DNA from the sample, wherein the sample is a blood, plasma or serum sample;
   (b) preparing a preparation of amplified DNA by performing PCR amplification on the cell-free DNA obtained in (a); and
   (c) analyzing the preparation of amplified DNA obtained in (b) to quantify an amount of total cf-DNA in the sample from the subject and determine whether the amount of total cf-DNA is equal to or exceeds a threshold total cf-DNA value of 8 ng/mL.

2. A method for preparing a preparation of amplified DNA from a sample from a transplant subject who is a heart transplant recipient for determining whether an amount of total cf-DNA is equal to or exceeds a threshold, the method comprising:
   (a) extracting cell-free DNA from the sample, wherein the sample is a blood, plasma or serum sample;
   (b) preparing a preparation of amplified DNA by performing PCR amplification on the cell-free DNA obtained in (a);
   (c) analyzing the preparation of amplified DNA obtained in (b) to quantify an amount of total cf-DNA in the sample from the subject and determine whether the amount of total cf-DNA is equal to or exceeds a threshold total cf-DNA value of 8 ng/mL; and
   (d) administering a treatment for a transplant complication to the subject of which the amount of total cf-DNA in the sample is equal to or exceeds the threshold total cf-DNA value, wherein the treatment is an anti-infection treatment, an anti-rejection treatment, or a cardiac arrest treatment.

3. The method of claim 1, wherein the subject is on or, is in need of, mechanical support.

4. The method of claim 2, wherein the transplant complication is cardiac arrest, infection or death.

5. The method of claim 1, wherein the amount of total cf-DNA is determined or obtained by:
   (a) for a plurality of single nucleotide variant (SNV) targets, performing an amplification-based quantification assay, such as a polymerase chain reaction (PCR) quantification assay, on the sample, or a portion thereof, with at least two primer pairs, wherein each primer pair comprises a forward primer and a reverse primer, wherein one of the at least two primer pairs comprises a 3' penultimate mismatch in a primer relative to one allele of the SNV target, but a 3' double mismatch relative to another allele of the SNV target and specifically amplifies the one allele of the SNV target, and another of the at least two primer pairs specifically amplifies to another allele of the SNV target, and
   (b) assessing the amount of total cf-DNA based on the results.

6. The method of claim 1, wherein the amount of total cf-DNA is determined or obtained using an amplification-based quantification assay or sequencing.

7. The method of claim 1, wherein an amount of total cf-DNA of 9 ng/mL or greater represents a risk of cardiac arrest or death.

8. The method of claim 1, wherein an amount of total cf-DNA of 20 ng/mL or greater represents the presence of an infection or an increased risk of infection.

9. A method for treating a transplant complication in a transplant subject who is a heart transplant recipient, the method comprising:
   (a) extracting cell-free DNA from a sample from the subject, wherein the sample is a blood, plasma or serum sample;
   (b) preparing a preparation of amplified DNA by performing PCR amplification on the cell-free DNA obtained in (a);
   (c) analyzing the preparation of amplified DNA obtained in (b) to quantify an amount of total cf-DNA in the sample from the subject and determine whether the amount of total cf-DNA is equal to or exceeds a threshold total cf-DNA value of 8 ng/mL; and
   (d) administering a treatment for a transplant complication to the subject of which the amount of total cf-DNA in the sample is equal to or exceeds the threshold total cf-DNA value, wherein the treatment is an anti-infection treatment, an anti-rejection treatment, or a cardiac arrest treatment.

* * * * *